(12) United States Patent
Shaw et al.

(10) Patent No.: US 8,777,504 B2
(45) Date of Patent: Jul. 15, 2014

(54) CLEANING TOOL

(75) Inventors: Thomas J. Shaw, Frisco, TX (US); Mark Small, Leonard, TX (US); Ni Zhu, Plano, TX (US); Steven E. Shaw, Frisco, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 1353 days.

(21) Appl. No.: 12/491,943

(22) Filed: Jun. 25, 2009

(65) Prior Publication Data

US 2010/0003067 A1    Jan. 7, 2010

Related U.S. Application Data

(63) Continuation-in-part of application No. 12/167,343, filed on Jul. 3, 2008, now abandoned.

(51) Int. Cl.
| | |
|---|---|
| B43K 5/00 | (2006.01) |
| B43K 8/06 | (2006.01) |
| A61M 35/00 | (2006.01) |
| A61M 39/16 | (2006.01) |
| A61B 19/00 | (2006.01) |

(52) U.S. Cl.
CPC ........... A61M 39/165 (2013.01); A61M 35/003 (2013.01); A61M 39/16 (2013.01); A61B 19/34 (2013.01); A61M 35/006 (2013.01)
USPC ........ 401/202; 401/132; 401/198; 15/104.93; 604/267

(58) Field of Classification Search
USPC ......... 401/196, 198, 202, 205, 262, 132, 133, 401/183, 186; 604/2, 3, 267; 15/104.93, 15/104.94, 160
See application file for complete search history.

(56) References Cited

U.S. PATENT DOCUMENTS

| | | | | |
|---|---|---|---|---|
| 2,307,044 | A | * | 1/1943 | Huston ......................... 401/186 |
| 2,975,464 | A | * | 3/1961 | Schultz ......................... 401/199 |
| 3,369,543 | A | * | 2/1968 | Ronco ............................... 604/2 |
| 3,694,845 | A | | 10/1972 | Engelsher |
| 3,860,348 | A | * | 1/1975 | Doyle ............................... 401/6 |
| 4,439,884 | A | | 4/1984 | Giorni |
| 4,440,207 | A | * | 4/1984 | Genatempo et al. .......... 150/154 |
| 4,446,965 | A | * | 5/1984 | Montiel ........................ 206/205 |
| 4,446,967 | A | | 5/1984 | Halkyard |
| 4,517,702 | A | | 5/1985 | Jackson |
| 4,784,647 | A | | 11/1988 | Gross |

(Continued)

FOREIGN PATENT DOCUMENTS

| | | |
|---|---|---|
| JP | 11361754 | 12/1999 |
| JP | 2001-309973 | 11/2001 |
| WO | WO 01/10285 | 2/2001 |

*Primary Examiner* — David Walczak
*Assistant Examiner* — Jennifer C Chiang
(74) *Attorney, Agent, or Firm* — Ross Barnes LLP; Monty L Ross; Robin L Barnes

(57) ABSTRACT

A tool that is useful for cleaning and disinfecting the attachment surfaces of a fluid connector device used in medical applications, the tool having a housing with an opening of defined shape and a chemically treated flexible insert positionable inside the housing that substantially conforms to the inside wall of the housing and, when placed over the attachment surfaces of a fluid connector device, can be manipulated axially and rotationally relative to the attachment surfaces to contact, clean and disinfect the surfaces. Some embodiments can also be used for topical cleaning of skin or other surfaces.

17 Claims, 17 Drawing Sheets

(56) References Cited

U.S. PATENT DOCUMENTS

| | | | | |
|---|---|---|---|---|
| 4,866,806 A | | 9/1989 | Bedford | |
| 4,893,956 A | * | 1/1990 | Wojcik et al. | 401/130 |
| 5,018,237 A | | 5/1991 | Valley | |
| 5,054,948 A | * | 10/1991 | Honda et al. | 401/196 |
| 5,137,524 A | | 8/1992 | Lynn et al. | |
| 5,382,297 A | | 1/1995 | Valentine et al. | |
| 5,514,117 A | | 5/1996 | Lynn | |
| 5,541,135 A | | 7/1996 | Pfeifer et al. | |
| 5,616,135 A | | 4/1997 | Thorne et al. | |
| 5,962,011 A | * | 10/1999 | DeVillez et al. | 424/448 |
| D449,909 S | | 10/2001 | Randolph et al. | |
| 6,349,443 B1 | | 2/2002 | Randolph et al. | |
| 6,692,173 B2 | * | 2/2004 | Gueret | 401/202 |
| 7,124,465 B1 | | 10/2006 | Kaminstein | |
| 7,225,814 B2 | * | 6/2007 | Barclay | 132/74.5 |
| 7,478,962 B2 | * | 1/2009 | De Laforcade | 401/262 |
| 8,065,773 B2 | * | 11/2011 | Vaillancourt et al. | 15/104.94 |
| 2007/0093762 A1 | | 4/2007 | Utterberg et al. | |
| 2007/0112333 A1 | | 5/2007 | Hoang et al. | |
| 2007/0225660 A1 | | 9/2007 | Lynn | |
| 2007/0292195 A1 | | 12/2007 | May et al. | |
| 2008/0019889 A1 | | 1/2008 | Rogers et al. | |
| 2008/0038167 A1 | | 2/2008 | Lynn | |
| 2008/0039803 A1 | | 2/2008 | Lynn | |
| 2008/0107564 A1 | | 5/2008 | Sternberg et al. | |
| 2009/0028750 A1 | * | 1/2009 | Ryan | 422/28 |
| 2010/0000040 A1 | | 1/2010 | Shaw et al. | |
| 2011/0044749 A1 | * | 2/2011 | Rossi | 401/205 |

\* cited by examiner

FIG. 12
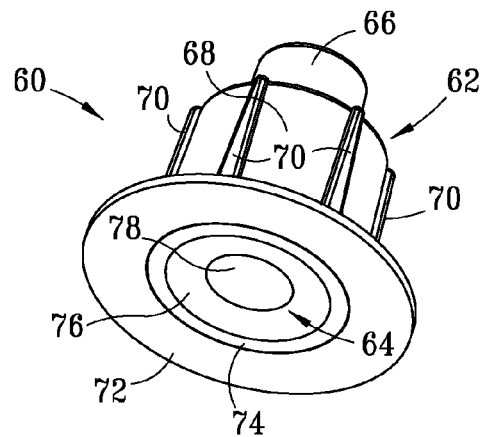
FIG. 14
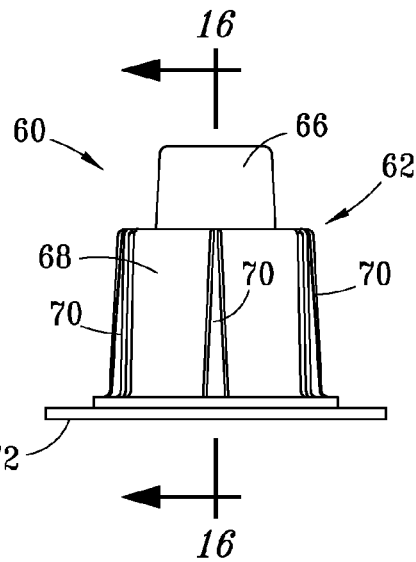
FIG. 13
FIG. 15
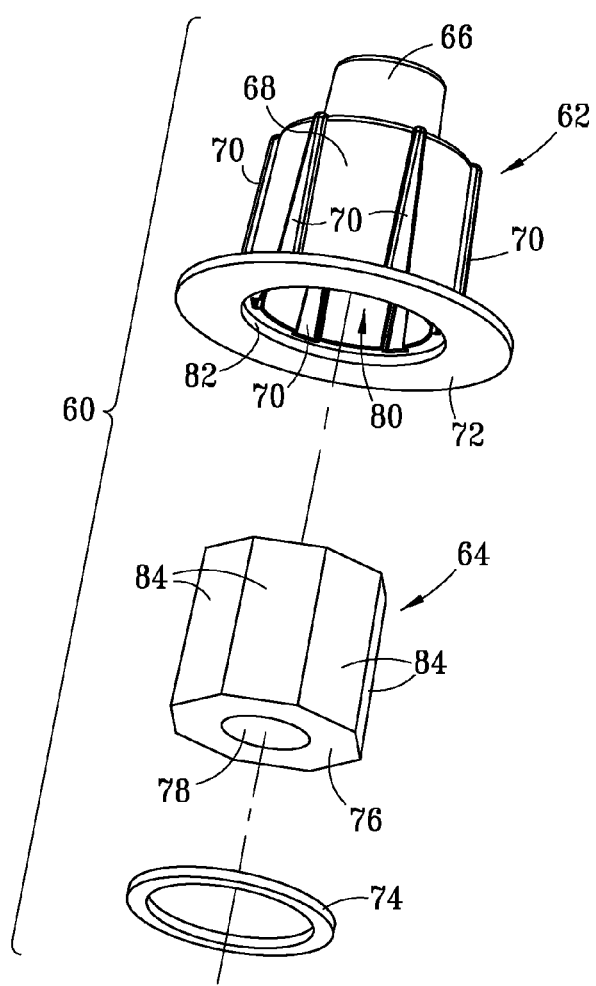

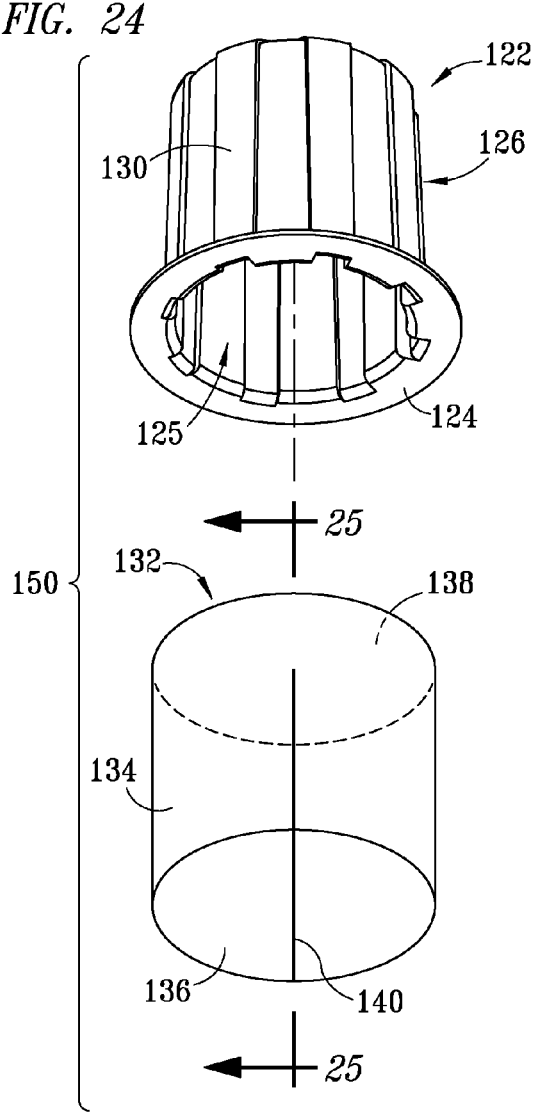
FIG. 24
FIG. 25
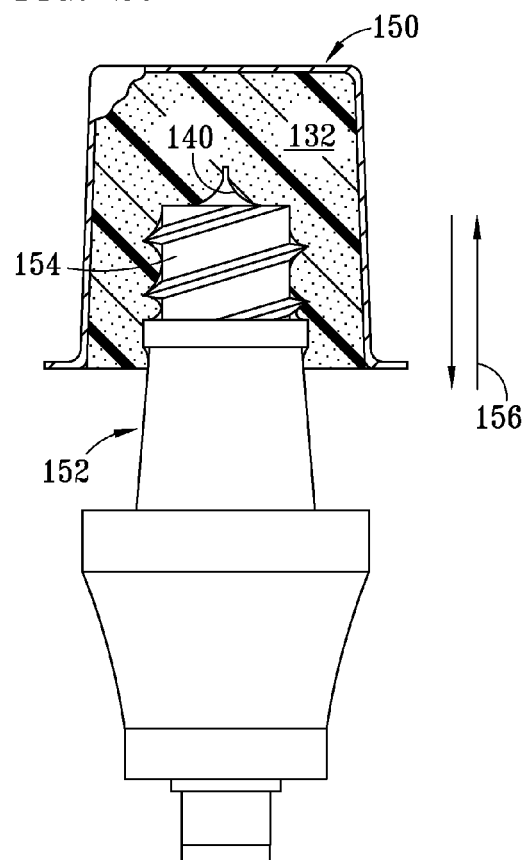
FIG. 26

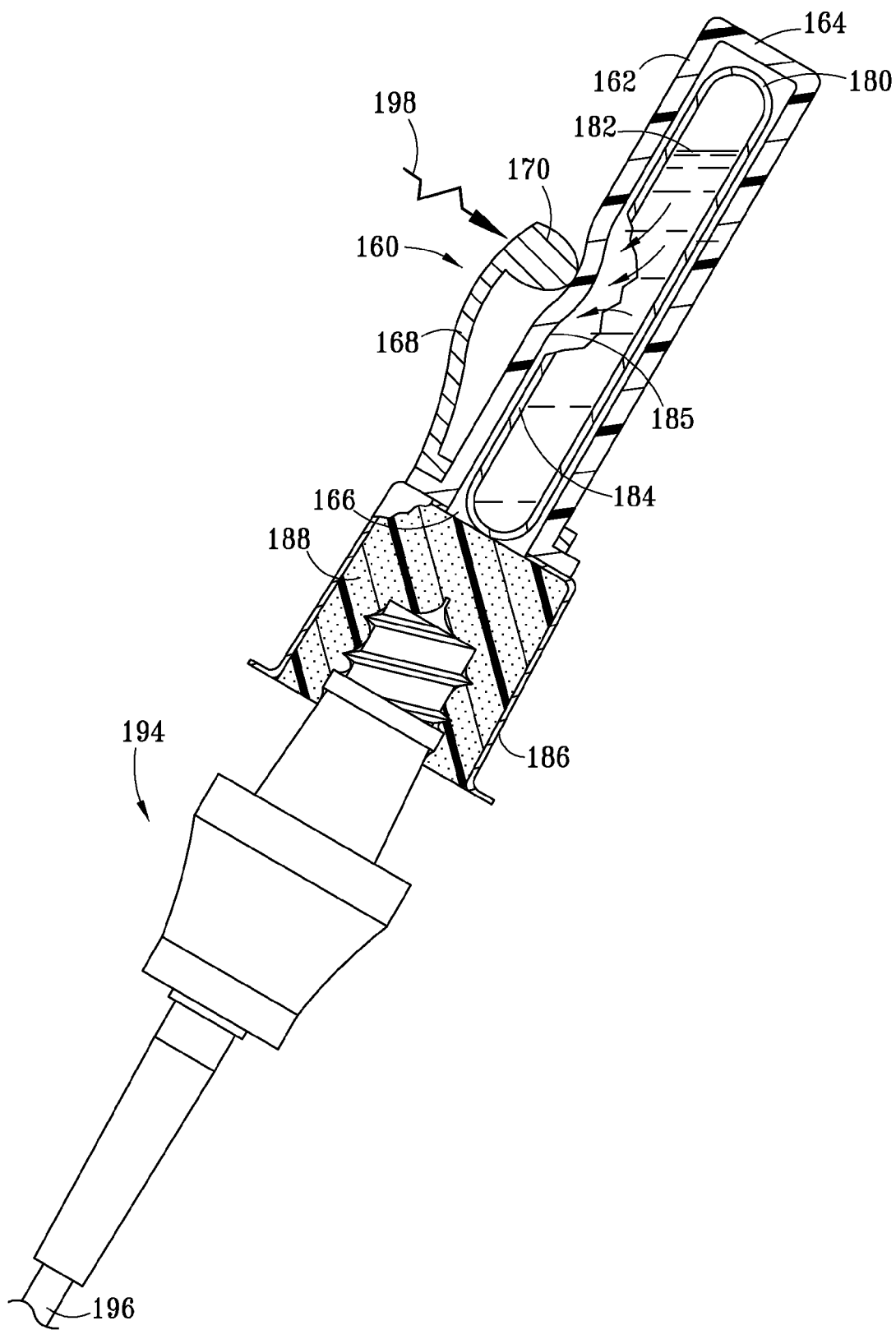

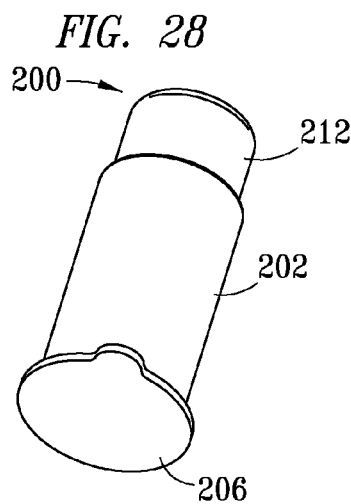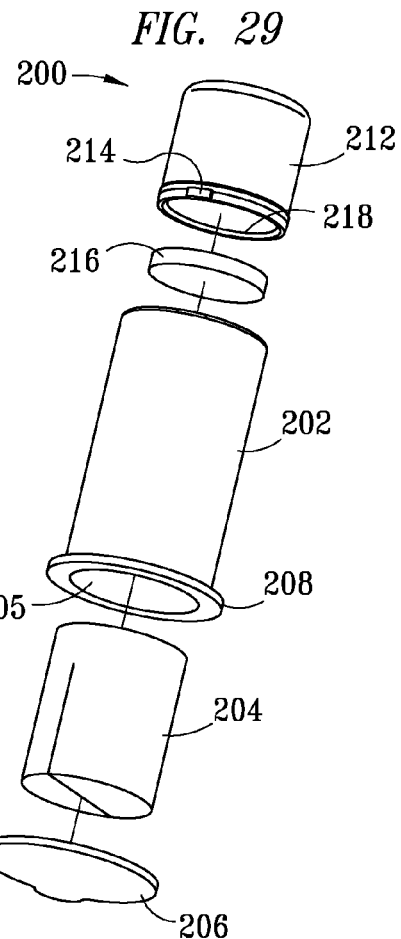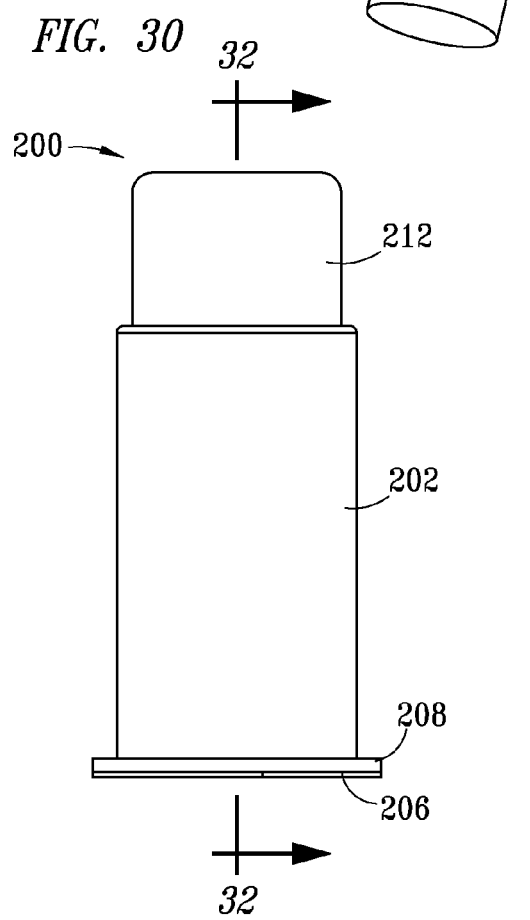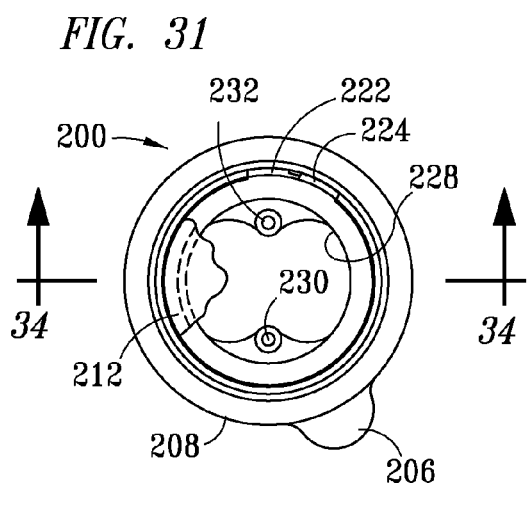

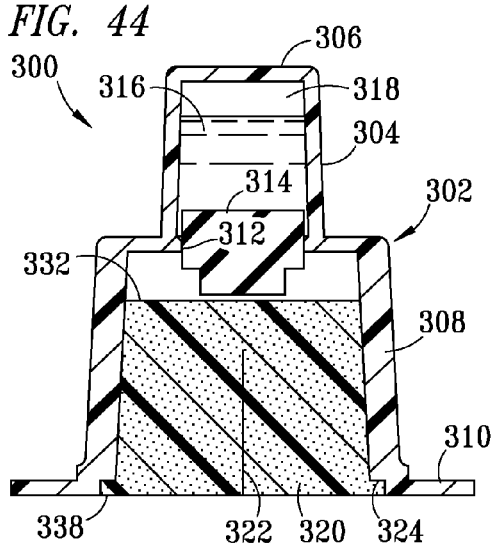
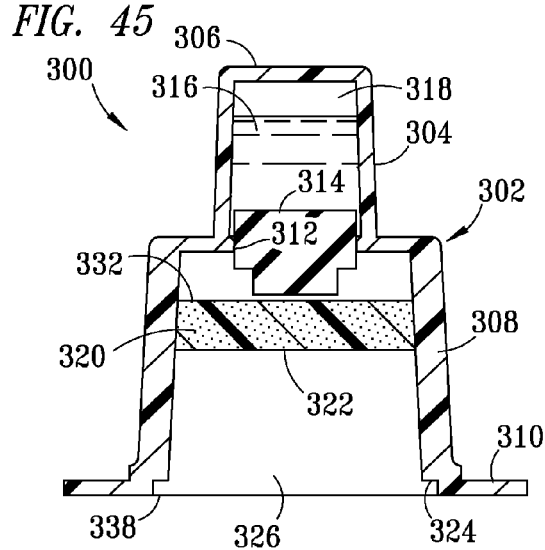
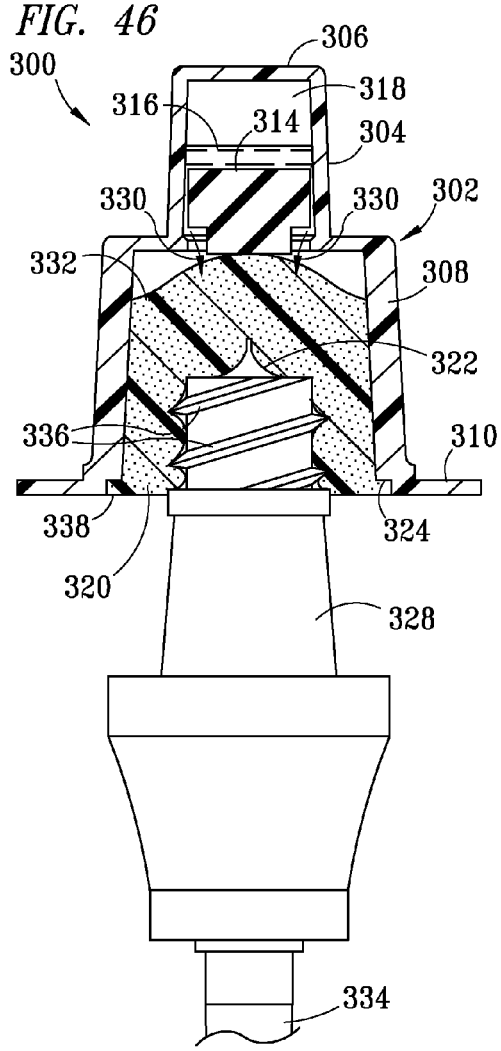
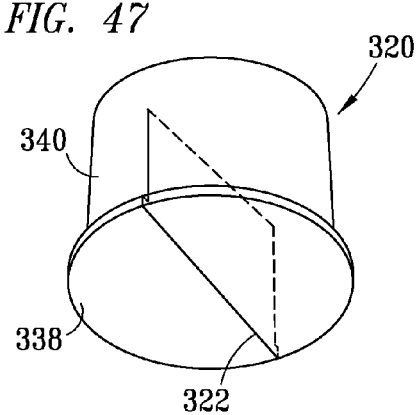
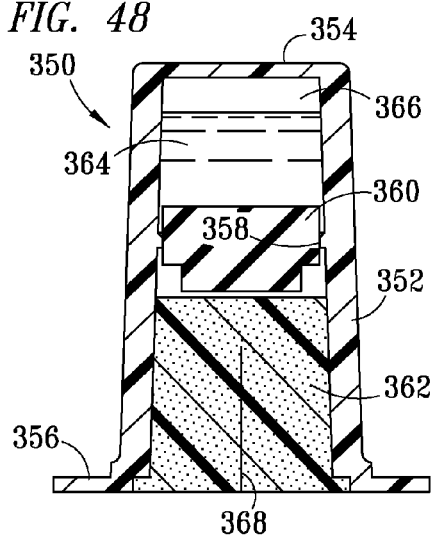

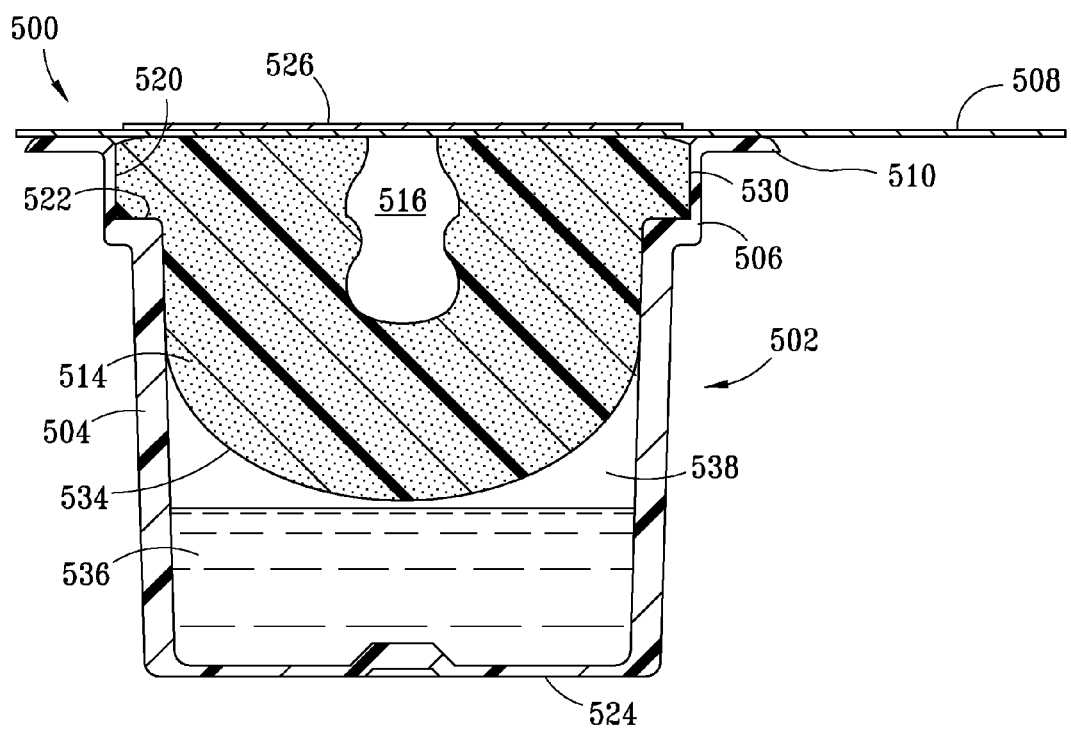
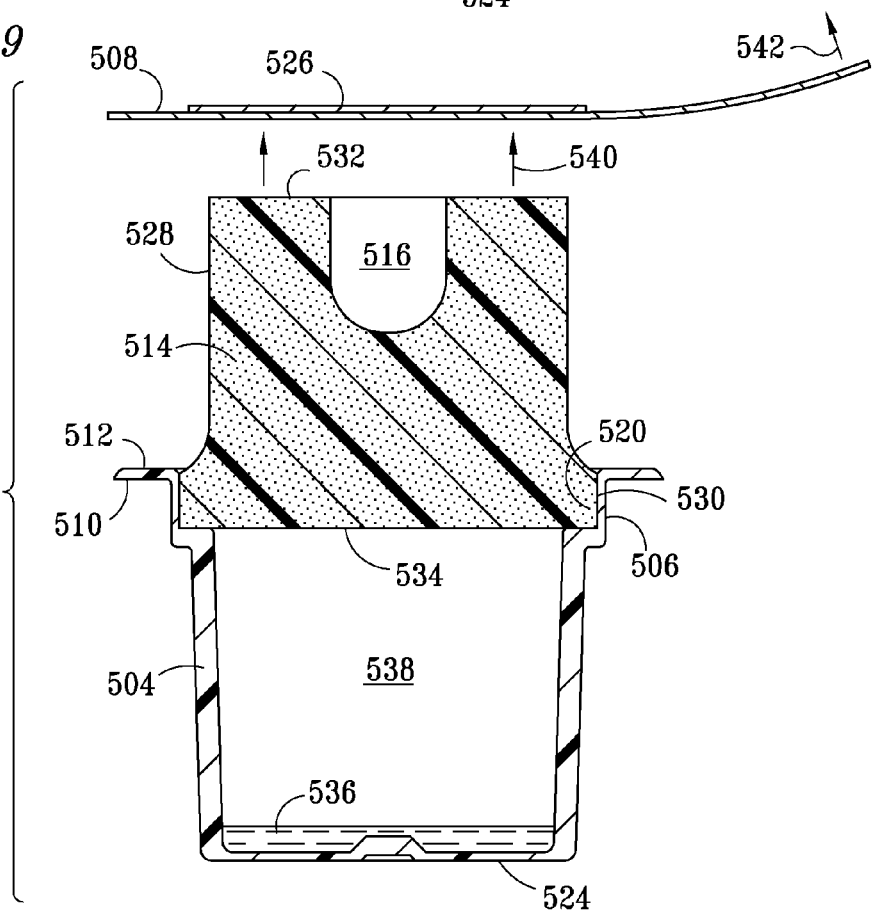

CLEANING TOOL

CROSS-REFERENCE TO RELATED APPLICATION

This application is a continuation-in-part of U.S. patent application Ser. No. 12/167,343, filed Jul. 3, 2008, now abandoned and priority is hereby claimed as to all common subject matter disclosed herein.

BACKGROUND OF THE INVENTION

1. Field of the Invention

This invention relates to a tool that is useful for mechanical cleaning and/or application of fluids to an exposed or accessible attachment surface of a fluid connector device used in medical applications.

2. Description of Related Art

A significant problem that exists today in the delivery of healthcare services is the accidental transmission of pathogens and diseases from one patient to another, or from a patient or healthcare worker to another, by improperly or inadequately cleaned connectors such as those used in fluid infusion or extraction therapies. Proper and thorough cleaning of fluid connector devices and ports is essential, for example, in reducing the incidence of methycillin-resistant *Staphylococcus aureus* (MRSA) infections.

Fluid connectors of medical devices are commonly cleaned using wipes that are saturated with alcohol or another similarly effective disinfectant. The wipes are manufactured and stored in sealed pouches until the time of use, then removed manually by the user, who holds the wipe in his or her fingers and rubs the wipe against the exposed surfaces of the attachment surfaces to be cleaned. Any bacteria or pathogen that is present on the fingers of the user, typically a healthcare worker who has also been treating other patients, can be transferred to the wipe and then to the attachment surfaces of the device, or can be transferred directly to the device by inadvertent contact between the user's hand and an attachment surface. Also, because fluid connectors of the attachment devices frequently comprise a plurality of differing surfaces having various contours and degrees of exposure, a conventional wipe may not reach all portions of the surfaces when manipulated by the user. This is particularly true, for example, where the fluid connector comprises threads.

An improved cleaning tool for the attachment surfaces of fluid connectors used in medical applications is therefore needed that will reduce the likelihood of direct contact between the hands of the user and the surface being cleaned, that will better conform to the contours of the attachment surfaces when manipulated by the user, and that will apply pressure more evenly around the perimeter of the fluid connector being cleaned.

Swab pouches have recently been disclosed in United States Patent Publication Nos. 2007/0225660 A1, 2008/0038167 A1 and 2008/0039803 A1 for use in covering, protecting and disinfecting the ends of luers, luer valves, cannulas and the like. Although such pouches offer some advantages over conventional wipes, a device is still needed that can be manufactured reliably and that can be manipulated easily and effectively by a clinician to mechanically scrub and/or disinfect exposed or accessible attachment surfaces of fluid connectors used in medical applications.

SUMMARY OF THE INVENTION

A tool is disclosed that is useful for mechanically cleaning and/or applying fluids to an exposed or accessible attachment surface of a fluid connector device used in medical applications. As used herein, "fluid" is intended to include liquids, gases, and solutions, suspensions or slurries. Such fluids can include or contain, for example, vascular and/or non-vascular fluids, medicines or flowable cellular tissues, that are infused into, or extracted or collected from, a patient. As used herein, "fluid connectors" or "fluid connector devices" can include, for example, luers, hubs, threaded or unthreaded connectors, Clave® connectors, and the like. Medical applications involving fluid infusion or extraction can include, for example, intravascular, intraosseous, intracranial, hepatic, lymphatic, subcutaneous, epidural, or urinary therapies. It should be understood and will be appreciated, however, by those of ordinary skill in the art upon reading this disclosure that these examples of fluids, fluid connector devices and medical applications are not exhaustive of those in connection with which the cleaning tool of the invention can be used beneficially.

According to one preferred embodiment of the invention, a cleaning and disinfecting tool is disclosed that preferably comprises a housing having an inside wall and an open end with a defined shape, and a flexible insert such as a sponge or other similarly effective material conforming substantially to inside wall of the housing that can be used to scrub and treat a frontal attachment with a suitable cleaner or disinfectant. The cleaning and disinfecting tool can be prepackaged in a sterile wrapper and, when removed from the package, placed over the attachment surfaces of a fluid connector device such as the attachment end of a CLAVE® connector. The cleaning and disinfecting tool can be manipulated axially and rotationally relative to the end of the frontal attachment to scrub the contacted surfaces of the connector and to apply a chemical capable of cleaning, disinfecting or otherwise decontaminating the contacted surfaces.

According to another preferred embodiment of the invention, the housing of the subject cleaning tool is molded, thermoformed or stamped from a suitable material, most preferably a polymeric material. A flexible insert such as a chemically treated sponge is preferably disposed inside the housing and can further comprise a centrally disposed opening having interior side and end wall sections configured to receive and contact external portions of the free end of a frontal attachment as the cleaning tool is manipulated by a user. Where the flexible insert is a sponge, the sponge desirably contains an amount of cleaner or disinfectant and, optionally, one or more other additives, that is adequate for decontaminating the frontal attachment with which it is used. Both the housing and the sponge portion of the cleaning tool are desirably latex-free to avoid possible allergic reactions with either the user or a patient.

According to another preferred embodiment of the invention, a cleaning and disinfecting tool for attachment surfaces of fluid connector devices used in medical applications is provided that comprises a housing with a defined open end and a flexible insert disposed inside the housing, the insert further comprising a cleaning or disinfecting composition that is released or releasable upon contact with one or more attachment surfaces of a fluid connector. The flexible insert can be unitarily formed or can be assembled from a plurality of elements, which elements can be either fixed or moveable relative to each other. The flexible insert can be made with or without a centrally disposed recess adapted to receive one or more attachment surfaces of a fluid connector. The flexible insert is preferably heat-staked to the inside of the housing, but can also be attached by use of any available adhesive, welding technique or other attachment method that is suitable for use with the materials and methods utilized for making the housing, flexible insert and cleaner or disinfectant.

According to another preferred embodiment of the invention, a cleaning tool for attachment surfaces of fluid connector devices used in medical applications is provided that comprises a housing containing a flexible insert as described above, and has an attached polymeric handle with flexible side walls, a closed end and a hollow interior cavity with an open end that is in fluid communication with the flexible insert. The frangible ampule or another similarly effective fluid reservoir is desirably disposed inside handle and preferably contains an amount of cleaning and disinfecting fluid that is sufficient to partially saturate flexible insert and effectively clean and disinfect the exposed free end of a frontal attachment inserted into surrounding contact by the insert. A lever arm with a blunt edge is desirably provided on the outside of the handle to facilitate the selective application of manual force against the side wall of handle, causing it to flex sufficiently to cause fracturing of the relatively rigid sidewalls of the ampule, thereby releasing cleaning and disinfecting fluid to flow downwardly by gravity into the flexible insert.

According to another preferred embodiment of the invention, a tool for mechanically cleaning and/or applying fluid to attachment surfaces of fluid connector devices used in medical applications is provided that comprises a generally cylindrical housing having two distinct cavities, one forwardly facing and the other rearwardly facing, with open ends and with an opening establishing fluid communication between them. A compressible, flexible insert preferably having a cellular internal structure is secured inside the forwardly facing cavity. Another substantially cylindrical receptacle having a closed rearwardly facing end and an open forwardly facing end sealed with a removable closure slidably engages the open end of the rearwardly facing housing cavity. The housing and receptacle are desirably cooperatively configured so that an application of force to the closed, rearwardly facing end of the receptacle will cause projecting prongs to dislodge the closure. When this occurs, a cleaning and/or disinfecting fluid such as isopropyl alcohol or chlorhexidine that is stored in the receptacle can flow either by gravity flow or by a piston effect as described below to saturate the flexible insert immediately prior to contacting the insert with the attachment surfaces of the fluid connector device being cleaned.

According to another preferred embodiment of the invention, a tool for mechanically cleaning and/or applying fluid to attachment surfaces of fluid connector devices used in medical applications is provided that comprises: a generally cylindrical housing, two flexible polymeric foam inserts, a liquid cleaner, and a releasable cover. The housing further comprises one closed end, one open end and sidewalls (most preferably fluted) that taper outwardly between the closed and an annular recess disposed adjacent to the open ends, with a substantially horizontal, annular flange disposed around the open end adjacent to the annular recess. The inserts include two substantially cylindrical, flexible foamed inserts insertable into the housing and capable of absorbing liquid and then expelling liquid when subsequently compressed; and a flexible sealing web substantially impervious to fluid migration through the web, said web being releasably attachable to the annular flange disposed around the open and further comprising a tab overhanging the flange on at least one side to facilitate manual grasping for removal. One flexible foam insert is desirably insertable into the housing below the annular recess and is maintained therein by any suitable means, most preferably by heat staking to prevent the insert from rotating freely inside the housing during use. That insert preferably comprises a slit or void capable of receiving an attachment surface of a fluid connector for cleaning and scrubbing. The other insert is preferably disk-shaped, has a slightly larger diameter, and is secured in substantially fixed relation to the underside of the web in such position that the insert is insertable into the annular recess adjacent to the open end of the housing when the web is releasably sealed to the annular flange of the housing. A therapeutically effective amount of a cleaning and/or disinfecting fluid is desirably placed inside the housing prior to applying the sealing web as a closure for the device. Upon removal of the web just prior to use, the liquid-containing disk-shaped insert attached to the underside of the web can be used for topical cleaning of skin, an exposed surface of an object, or an attachment surface of a fluid connector as desired in addition to use of the liquid-containing flexible insert disposed inside the housing.

According to another preferred embodiment of the invention, another tool is disclosed that can be used for both topical cleaning of skin or an exposed surface, and for mechanically cleaning and/or applying fluid to attachment surfaces of fluid connector devices used in medical applications. The subject tool preferably comprises structural elements as described in Paragraph 0012 above except that it desirably comprises only a single, liquid-absorbing, flexible foamed polymeric insert having a cylindrical base that is preferably heat-staked into the annular recess of the housing. The upwardly projecting portion of the insert preferably further comprises a slit or recess to facilitate use as a cleaning tool for attachment surfaces of fluid connector devices used in medical applications. Prior to sealing, the insert projects upwardly past the otherwise open end of the housing. Prior to heat-staking, a cleaning and/or disinfecting liquid is desirably introduced into the housing. After attachment of the insert to the annular recess of the housing, the flexible foam insert is desirably compressed inside the housing and the web is releasably sealed to the flange to cover the opening and maintain the insert in its compressed state pending use. When the web is later removed just prior to use, and the insert is substantially saturated with the cleaning liquid, the insert expands to its projecting position to facilitate use as a topical cleaning or disinfecting tool. The slit or recess in the upwardly facing portion of the insert can receive at least a portion of the attachment surfaces of a fluid connector or outer surfaces of another device, and the upwardly projecting portion of the insert can be forced back down inside the housing, where the sidewalls provide resistance and facilitate scrubbing the attachment surfaces.

BRIEF DESCRIPTION OF THE DRAWINGS

The apparatus of the invention is further described and explained in relation to the following drawings wherein:

FIG. 12 is a perspective view of another embodiment of a preferred tool useful for cleaning and disinfecting the exposed attachment surfaces of a fluid connector device such as, for example, a CLAVE® connector, to another medical device such as, for example, a needleless syringe;

FIG. 13 is an exploded perspective view illustrating the component parts of the tool of FIG. 12;

FIG. 14 is a front elevation view of the tool of FIG. 12;

FIG. 15 is a bottom plan view of the tool of FIG. 12;

FIG. 24 is an exploded bottom perspective view of a cleaning tool made using the housing of FIG. 21 in combination with a flexible insert;

FIG. 25 is a cross-sectional elevation view taken along line 25-25 of FIG. 24;

FIG. 26 is a front elevation view, partially in section, of the tool of FIG. 24 being used to clean and disinfect the attachment surfaces of a fluid connector;

FIG. 27 is an inclined view, partially in section, of another embodiment of the subject cleaning tool being used to clean and disinfect the attachment surfaces of a fluid connector, the tool comprising a handle with a reservoir containing a cleaning and disinfecting composition that is selectively releasable into the flexible insert;

FIG. 28 is a perspective view of another embodiment of the subject cleaning tool;

FIG. 29 is an exploded perspective view of the cleaning tool of FIG. 28;

FIG. 30 is a front elevation view of the cleaning tool of FIG. 28;

FIG. 31 is a top plan view, partially broken away, of the cleaning tool of FIG. 28;

FIG. 44 is a is a cross-sectional front elevation view of a preferred embodiment of another cleaning tool of the invention;

FIG. 45 is a cross-sectional front elevation view of the cleaning tool of FIG. 44 that is taken transversely to the cross-sectional view in FIG. 44;

FIG. 46 is a cross-sectional front elevation view of the cleaning tool of FIG. 44 being used to clean the attachment end of a fluid connector;

FIG. 47 is a bottom perspective view of a flexible insert as shown in FIGS. 44-46;

FIG. 48 is a cross-sectional front elevation view of a preferred embodiment of another cleaning tool of the invention;

FIG. 58 is an enlarged cross-sectional view taken along line 58-58 of FIG. 56; and FIG. 59 is an exploded view as in FIG. 58 but showing the closure web displaced above the housing and the liquid-saturated compressible foam insert projecting upwardly from the housing.

DESCRIPTION OF THE PREFERRED EMBODIMENTS

Figure 1:
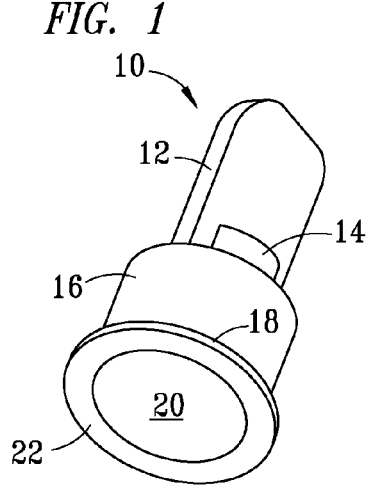
FIG. 1 is a perspective view of one embodiment of a housing that is part of a preferred tool useful for cleaning and disinfecting the exposed attachment surfaces of a frontal attachment device such as, for example, a CLAVE® connector, to another medical device such as, for example, a needleless syringe.
Figure 2:
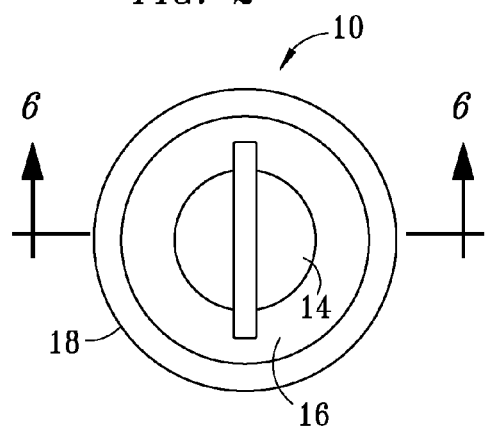
FIG. 2 is a top plan view of the housing of FIG. 1.
Figure 3:
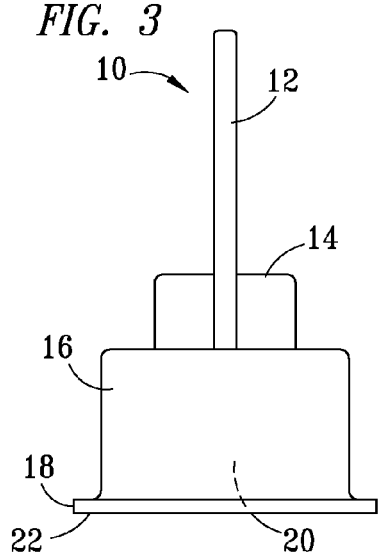
FIG. 3 is a front elevation view of the housing of FIG. 1.
Figure 4:
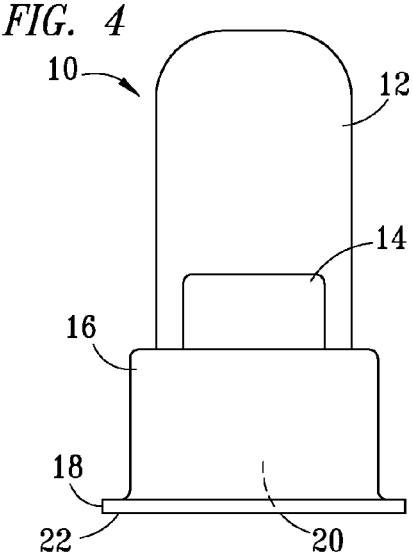
FIG. 4 is a side elevation view of the housing of FIG. 1.
Figure 5:
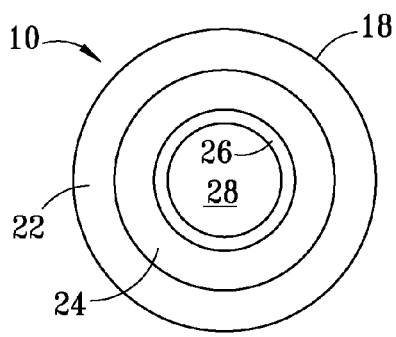
FIG. 5 is a bottom plan view of the housing of FIG. 1.
Figure 6:
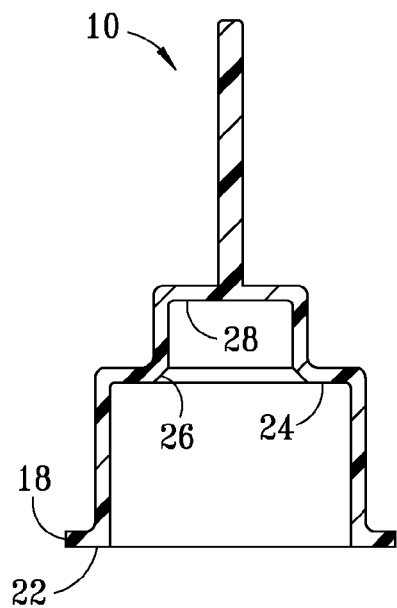
FIG. 6 is a cross-sectional elevation view taken along line 6-6 of FIG. 2.
Figure 7:
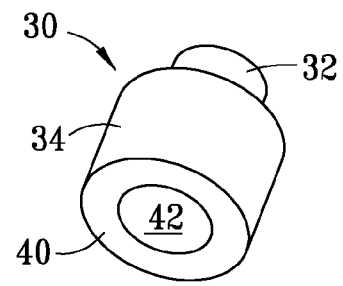
FIG. 7 is a perspective view of one embodiment of a preferred chemically treated cleaning sponge that is insertable into and attachable to the housing of FIG. 1.
Figure 8:
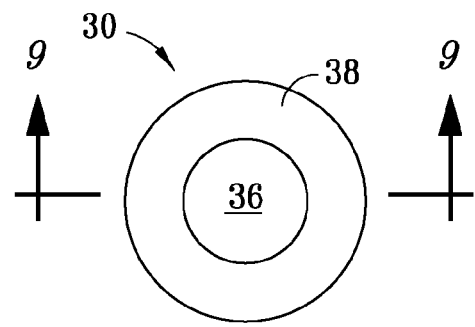
FIG. 8 is a top plan view of the chemically treated cleaning sponge of FIG. 7.

Referring to FIGS. 1-6, a preferred embodiment of the cleaning and disinfecting tool of the invention comprises housing 10 that is preferably unitarily molded, stamped or thermoformed from a polymeric composition, thin metallic material or laminate. If molded or thermoformed, housing 10 preferably comprises a polymeric material that can be glued or sonically welded. Housing 10 preferably further comprises projecting tab or handle 12 that is easily graspable by a user, and a substantially cylindrical body having coaxially aligned upper body section 14 and adjacent lower body section 16. It should be appreciated that "substantially cylindrical," as used in this disclosure, can include sections having different inside or outside diameters and such slopes or tapers as may be needed or appropriate in view of the particular configuration and the method and material of construction that are used in making housing 10. Taken together, upper and lower sections 14, 16 define an open interior space 20 having a stepped inside diameter, with upper section 14 preferably having an inside diameter that is less than the inside diameter of lower section 16. Lower section 16 preferably comprises an open end opposite upper section 14 that is surrounded and stabilized by flange 18 having annular face 22. Upper body section 14 further comprises closed end wall 28 connected to handle 12. The transition between upper and lower body sections 14, 16 is preferably defined by inclined annular shoulder 26 at the interior edge of annular stop surface 24.

Figure 10:
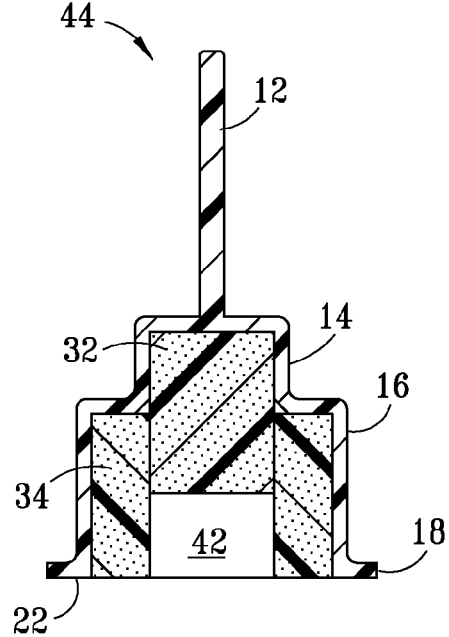
FIG. 10 is a cross-sectional elevation view of a preferred embodiment of the cleaning and disinfecting tool of the invention.

Referring to FIG. 10, a preferred embodiment of tool 44 of the invention is made by inserting and preferably securing a flexible insert such as a compressible sponge 30 inside open interior space 20 of the cylindrical body of housing 10, as discussed above in relation to FIGS. 1-6. Sponge 30 can be secured inside opening 20 of housing 10 by any suitable means such as, for example, by use of an adhesive. Desirably, sponge 30 will be constrained inside housing 10 sufficiently that sponge 30 (and especially its outside wall) will not be easily rotatable or translatable relative to the inside walls of housing 10 once sponge 30 is installed. This will facilitate the use of rotational and axial movement of tool 44, applied through handle 12, to clean and scrub the exterior attachment surfaces of a frontal attachment device as described in greater detail below in relation to FIG. 11. Alternatively, it will be appreciated by those of ordinary skill in the art upon reading this disclosure that the structure of housing 10 can be modified by the addition of other structural elements to constrain the movement of sponge 30 relative to the inside walls of housing 10 frictionally and without the use of an adhesive if desired.

Referring again to FIGS. 10-11, sponge 30 preferably has a configuration that is receivable within the cylindrical body of housing 12, and that also comprises an opening having a defined shape into which the attachment surfaces at the free end of a frontal attachment device such as a CLAVE® connector are receivable for cleaning and disinfecting. Sponge 30 is desirably made of a compressible, open-cell material adapted to receive, retain and release a composition containing a disinfectant when sponge 30 is placed in contact with or compressed against an attachment surface of a frontal attachment device such as a CLAVE® connector. Most preferably, sponge 30 will comprise open-cell polyurethane foam or another similarly effective non-latex, open-cell material. The dimensions and configuration of sponge 30 are desirably such that sponge 30 can be positioned and secured snugly inside housing 10, and, with some compression, will receive and contact substantially all the surface area of the attachment surfaces of a frontal attachment device to promote cleaning and disinfecting of the attachment surfaces.

Although the flexible insert disposed inside the housing of the invention is principally referred to as a "sponge" throughout this disclosure, it should be appreciated by those of ordinary skill in the art upon reading this disclosure that other similarly effective molded, woven, porous or layered materials can likewise be used within the scope of the invention provided that such materials are capable of retaining prior to use and subsequently releasing during use an amount of cleaning chemical or disinfectant that is effective for decontaminating any contacted surfaces of a frontal attachment to a medical device with which the subject tool is used. In some cases it can be desirable for a cleaning agent or disinfectant to be adsorbed into or encapsulated in recesses or voids disposed inside the flexible insert of the invention.

Figure 9:
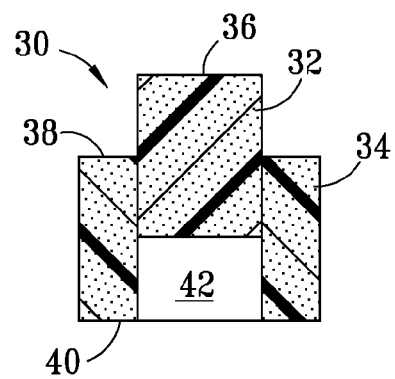
FIG. 9 is a cross-sectional elevation view taken along line 9-9 of FIG. 8.

Referring again to FIGS. 6-10, sponge 30 preferably comprises upper cylindrical section 32, lower cylindrical section 34, top surface 36 that abuts and can be adhered to end wall 28 of housing 10, annular surface 38 that abuts and can be adhered to annular stop surface 24 of housing 10 and interior space 42 having an opening defined by bottom surface 40 of lower cylindrical section 34. Although upper and lower cylindrical sections 32, 34, respectively, of sponge 30 are depicted in FIGS. 9 and 10 as being two distinct elements, it should be appreciated that they can be unitarily formed, or formed separately and joined by any suitable means known to those of ordinary skill in the art, such as, for example, by thermal or other welding techniques, by the use of commercially available adhesives, or the like. Alternatively, as discussed below in relation to FIGS. 12-17, the Referring to FIGS. 9-11, when tool 44 is removed from its own sterile wrapper, sponge 30 is preferably already impregnated, substantially saturated or coated with a sufficient amount of a disinfectant-containing composition, most preferably isopropyl alcohol or another similarly effective liquid or powder, to achieve a desired level of decontamination. Tool 44 is then preferably used by placing it over the attachment surfaces 48 of a frontal attachment device, such as a CLAVE® connector that is already connected by tubing 52 to an extension set or IV catheter (not shown). Once attachment surfaces 48 are disposed inside the interior space 42 of tool 40, the inwardly facing side and end walls of sponge 30 are desirably compressed sufficiently to contact all the external area of attachment surfaces 48, and upon compression, will release the disinfectant-containing composition disposed inside sponge 30 directly onto attachment surfaces 48. By grasping handle 12, tool 44 can then be manipulated by the user to scrub attachment surfaces 48 by reciprocating tool 48 in an axial direction as demonstrated by arrows 54 and rotationally as indicated by arrows 56. Such scrubbing is believed to provide better and more effective cleaning and disinfecting than is achievable using prior art alcohol wipes or napkins.

Although one embodiment of the apparatus of the invention that is particularly intended for use with the attachment surfaces of CLAVE® connectors is disclosed above, it will be appreciated that other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

For example, referring to FIGS. 12-17, another preferred embodiment of the invention is disclosed wherein cleaning and disinfecting tool 60 further comprises housing 62 and a flexible insert 64 that is retained inside housing 60 by retainer ring 74. Retainer ring 74 can be snapped or pressed into an annular recess 82 on the inside of flange member 72. In this embodiment, housing 62 comprises upper portion 66, lower portion 68 having a plurality of circumferentially spaced, radially extending ribs 70, and flange 72. The external portions of radially extending ribs 70 provide a gripping surface for the user, and the internal portions of ribs 70 assist in resists rotational movement of flexible insert 64 inside housing 62. Although lower portion 68 of housing 62 as shown is substantially cylindrical, it should be appreciated that housings having other polygonal cross-sections can likewise be used in the cleaning and disinfecting tools of the invention.

Figure 16:
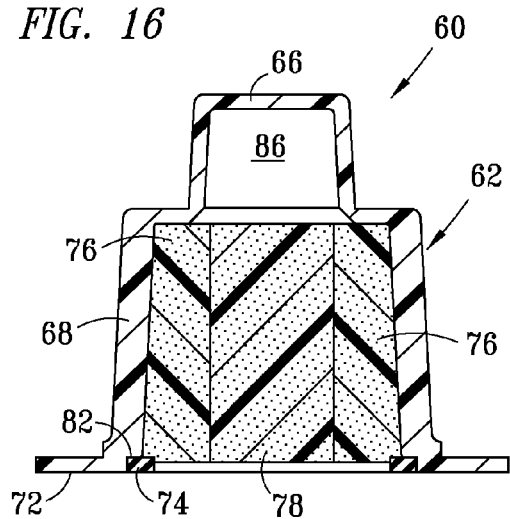
FIG. 16 is a cross-sectional elevation view taken along line 16-16 of FIG. 14, showing the central portion of the sponge in a first position.
Figure 17:
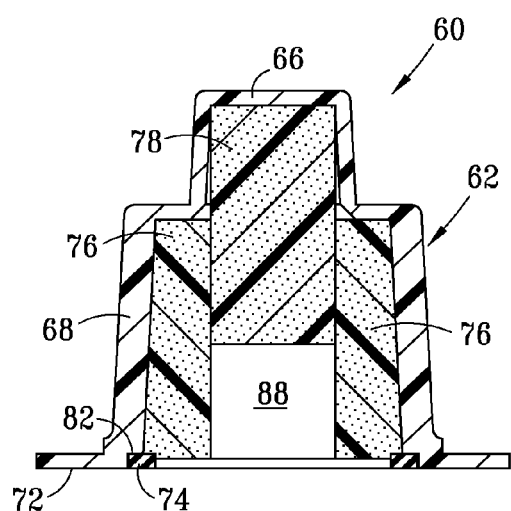
FIG. 17 is a cross-sectional elevation view substantially as shown in FIG. 16, but with the central portion of the sponge in a second position that is elevated in relation to the first position.

Referring to FIGS. 13, 16 and 17, flexible insert 64 comprises an outer section 76 having a centrally disposed cylindrical bore that is plugged by cylindrical element 78. Outer section 76 has an octagonal perimeter defined by a plurality of flat surfaces 84, each of which is preferably sized and configured to conform substantially to and cooperate with internal ribs 70 of housing 62 to resist rotational movement of outer section 76 relative to lower portion 68 of housing 62 as cleaning and disinfecting tool 60 is manipulated by a user while cleaning a frontal attachment. As with cleaning and disinfecting tool 44 described above in relation to FIG. 11, tool 60 is also desirably manipulated both axially and rotationally relative to a frontal attachment during use. Although a lower portion 76 having a hexagonal perimeter is a preferred structure for use in the invention, other polygonal configurations can also be used within the scope of the invention provided that any flexible insert so configured will conform substantially to and cooperate with the inside structure and configuration of the associated housing so that the resultant cleaning and disinfecting tool can function substantially as disclosed herein. Flexibility is desired to permit the surfaces that engage a frontal attachment during use to flex around and contact various portions of the frontal attachment.

Flexible insert 64 desirably comprises any suitable material substantially as disclosed above for use in making sponge 30 of the invention, and is desirably sufficiently compressible to be inserted into defined interior space 80 of housing 62. If desired, adhesive can also be used to help hold flexible insert 64 in place. Retainer ring 74 is desirably seated in annulus 82 of housing 62, and is preferably pressed or snapped into position to assist in maintaining outer section 76 of flexible insert 64 in a preferred axial position inside housing 62 during use. Retainer ring 74 can be made of rubber, plastic or metal, and can be continuous, contain a gap, or comprise projections or bosses that cooperate with housing 62 to retain ring inside annular recess 82.

Figure 11:
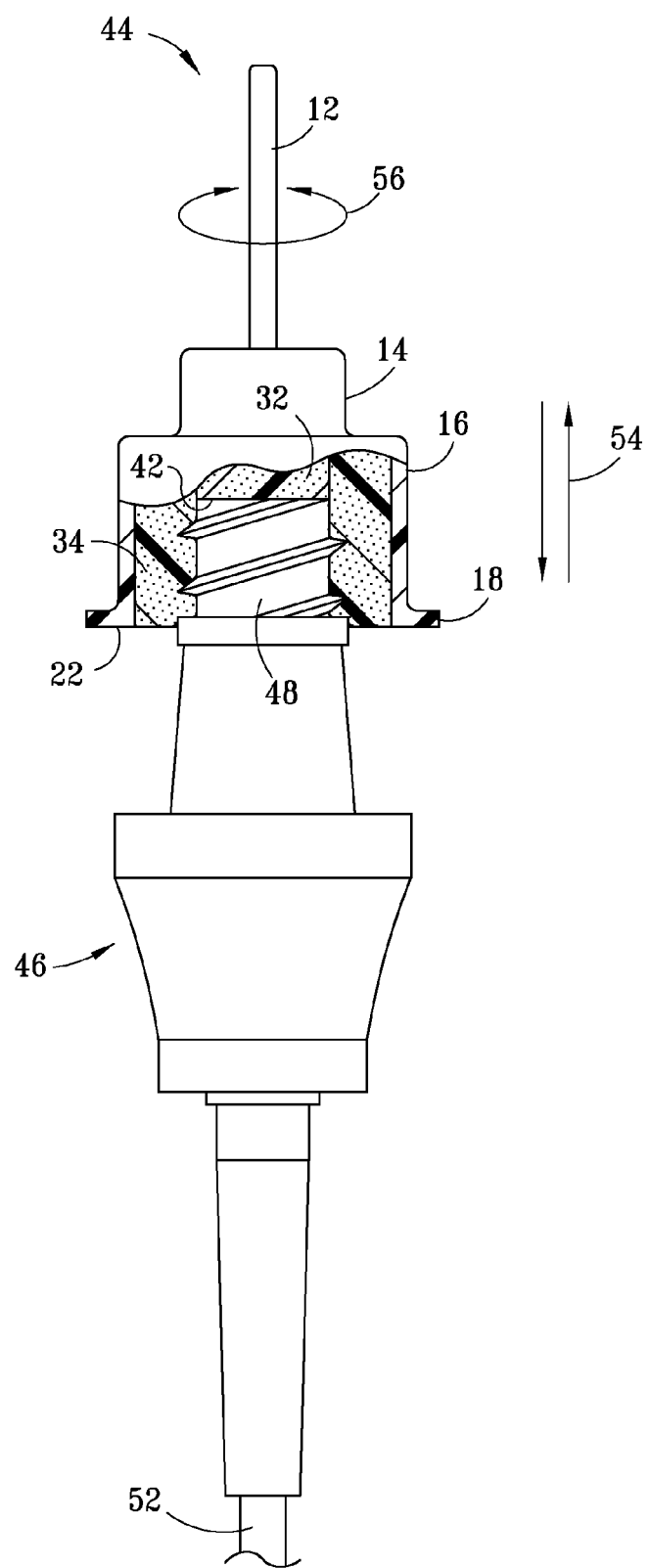
FIG. 11 is a front elevation view, partially in section and partially broken away, of the tool of FIG. 10 being used to clean and disinfect the attachment surfaces of a fluid connector device.

As shown in FIGS. 16 and 17, cylindrical element 78 is preferably made of the same flexible, compressible material as outer section 76 of flexible insert 64. As shown in FIG. 16, cylindrical element 78 is axially positioned so that its top and bottom ends are substantially flush with the corresponding ends of outer section 76, and interior 86 of upper portion 66 is open. Then, when cleaning tool 60 is pressed against the tip of a frontal attachment, cylindrical element 78 can slide upwardly relative to outer section 76 until cylindrical element 78 engages the closed end wall of upper portion 66. This provides a substantially cylindrical space 88 inside housing 62 where portions of flexible insert 64 face the frontal attachment on three sides in substantially the same way as is depicted in FIG. 11.

Figure 18:
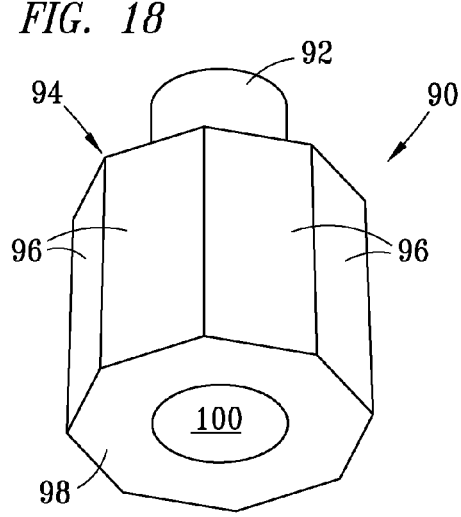
FIG. 18 is a perspective view of one embodiment of a preferred chemically treated cleaning sponge that is configured differently from the sponge depicted, for example, in FIG. 13.
Figure 19:
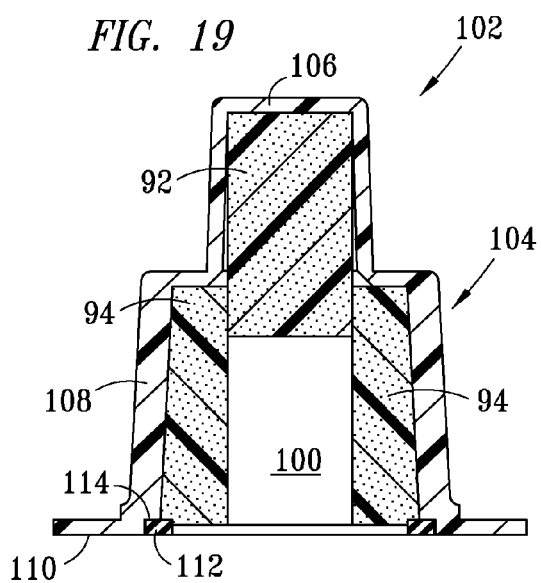
FIG. 19 is a cross-sectional elevation view of another embodiment of the preferred tool of the invention that is similar to the tool of FIG. 16 but includes a housing that is configured to receive a chemically treated cleaning sponge having a configuration like that of the sponge shown in FIG. 18.

Still another preferred embodiment of the invention is depicted and described in relation to FIGS. 18-19. Flexible insert 90 can be made of materials as described above in relation to other preferred flexible inserts or sponges of the invention, and like flexible insert 64, comprises an outer section 94 having a polygonal perimeter that is preferably sized and configured to cooperate with internal portions of housing 104 to resist rotational movement of outer section 94 relative to lower portion 108 of housing 104 as cleaning and disinfecting tool 102 is manipulated by a user while cleaning a frontal attachment. In this embodiment, however, cylindrical element 92 is initially disposed above the top of outer section 94, and a cylindrical open space 100 is disposed below it to receive a portion of a frontal attachment (not shown) that is inserted inside it during use. Cylindrical element 92 preferably seats against end wall 106 of housing 104, and can be unitarily made with outer section 94 or not, as desired.

As with cleaning and disinfecting tool 44 described above in relation to FIG. 11, tool 102 is also desirably manipulated both axially and rotationally relative to a frontal attachment during use. Although a lower portion 94 having a hexagonal perimeter comprising side walls 96 is a preferred structure for use in the invention, either cylindrical or other polygonal configurations can also be used within the scope of the invention for either the upper or lower portions of housing 104 provided that any flexible insert so configured will cooperate with the inside structure and configuration of the associated housing so that the resultant cleaning and disinfecting tool can function substantially as disclosed herein. Flexibility is desired to permit the surfaces that engage a frontal attachment during use to flex around and contact various portions of the frontal attachment. If desired, either element 92 or outer portion 94, or both can also be attached to the inwardly facing surface of sidewall 108 of housing 104. As with housing 62, side wall 108 of housing 104 can also function as a handle for use in manipulating cleaning and disinfecting tool 102 relative to a frontal attachment.

Figure 20:
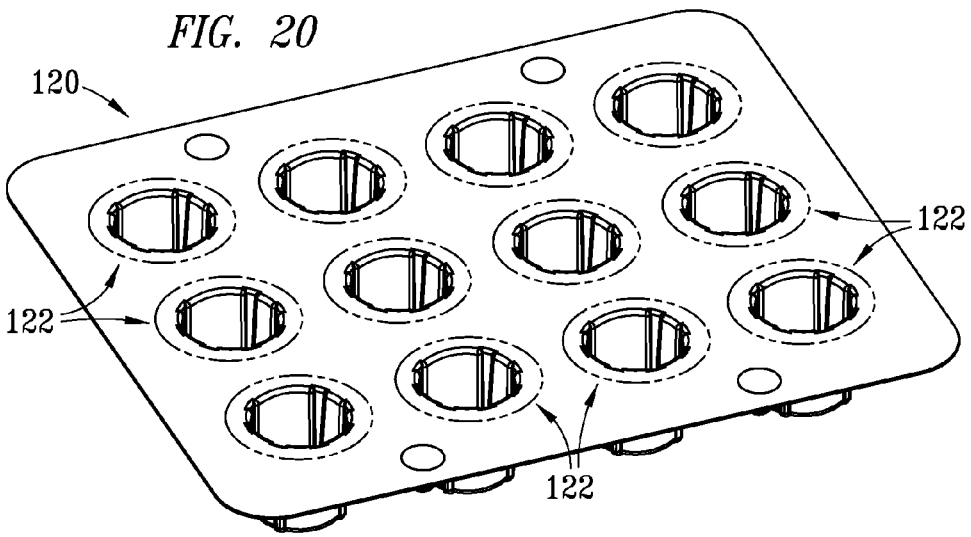
FIG. 20 is a top perspective view of an array comprising a plurality of housings suitable for use in making a preferred embodiment of the cleaning tool of the invention prior to separating them from a web connecting them during manufacture.
Figure 21:
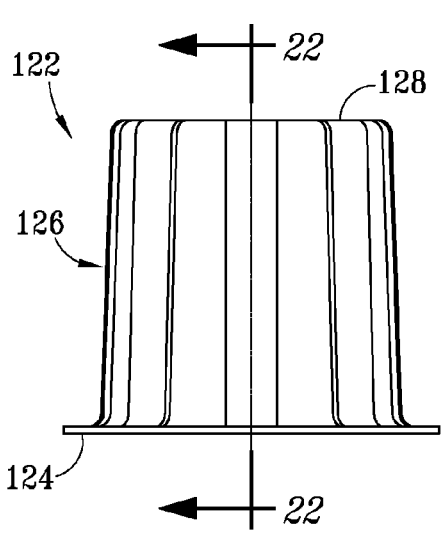
FIG. 21 is front elevation view of a single housing that has been inverted following separation from the array of FIG. 20.
Figure 22:
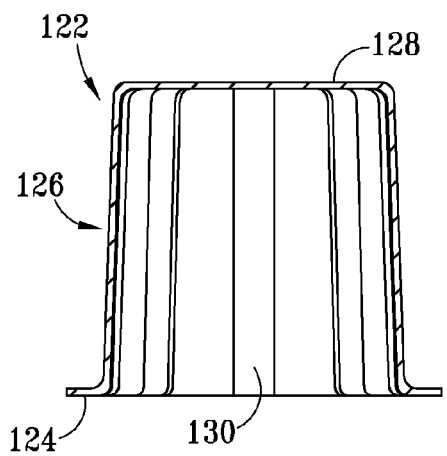
FIG. 22 is a cross-sectional elevation view taken along line 22-22 of FIG. 21.
Figure 23:
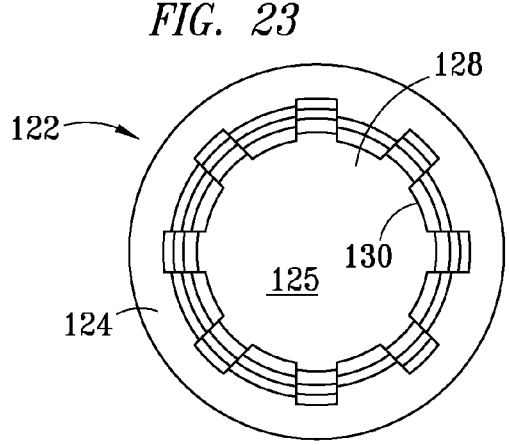
FIG. 23 is bottom plan view of the housing of FIG. 21.

FIG. 20 depicts an array 120 of polymeric housings 122 suitable for use in making an embodiment of the cleaning tool of the invention. As shown, housings 122 are interconnected by a substantially continuous web from which they can be separated by any suitable conventional method or device such as, for example, by die cutting around the phantom lines that are intended to represent the flange perimeters of each respective housing as described below. Depending upon the material of construction, the depth of each housing 122, and the side wall configuration of each, array 120 can be injection molded, thermoformed, or otherwise fabricated using known manufacturing methods. Referring to FIGS. 21-23, each housing 122 preferably further comprises annular flange 124 around an opening of defined shape, a continuous, substantially cylindrical side wall 126, bottom 128, and an inside wall comprising a plurality of flutes 130.

Referring to FIGS. 24-26, housing 122 as described above is desirably configured to receive a flexible insert 132, most preferably made from a resilient, spongy or elastomeric material having a side wall 134 that is compressible to facilitate insertion into interior space 125 of housing 122, whereupon side wall 134 desirably expands slightly to conform substantially to the inside wall of housing 122 and into engagement with flutes 130, or to be heat-staked to some portion of the wall, or to a shelf or other surface adjacent to the wall. Alternatively, other functionally equivalent methods of attachment, such as sonic welding, gluing or the like, can also be used. Where flexible insert 132 is attached to the wall, the presence of flutes or other irregularities on the surface of the inside wall are not needed to resist rotational movement of the insert inside the housing, although surface texturing on the outside can still be desirable to facilitate gripping. The insertion of flexible insert 132 into housing 122 forms cleaning tool 150, which can then be impregnated or at least partially saturated with a composition as previously described that is suitable for use in cleaning and disinfecting a frontal attachment. A slit 140 can be provided in facing surface 136 of flexible insert 132 and continuing upward to continuous web 144 to create opposed facing surfaces 142 that permit the insertion of frontal attachment 152 into cleaning tool 150 as shown in FIG. 26. As shown, frontal attachment 152 is a CLAVE® connector attached to tubing segment 158. The forwardly extending threaded portion of frontal attachment 152 is desirably cleaned by manipulating cleaning tool 150 up and down as indicated by opposed arrows 156, and by manually rotating cleaning tool 150 relative to frontal attachment 152.

Another preferred embodiment of the invention is disclosed in relation to FIG. 27. According to this embodiment of the invention, cleaning tool 160 is shown in relation to frontal attachment 194 attached to tubing segment 196. Cleaning tool 160 preferably further comprises a housing 186 containing a flexible insert 188, and has an attached polymeric handle 162 with flexible side walls, a closed end 164 and a hollow interior cavity with an open end 166 that is in fluid communication with flexible insert 188. Frangible ampule 180 or another similarly effective fluid reservoir is desirably disposed inside handle 162 and preferably contains an amount of cleaning and disinfecting fluid 182 that is sufficient to partially saturate flexible insert 188 and effectively clean and disinfect the exposed free end of frontal attachment 194. Lever arm 168 with blunt edge 170 is desirably provided on the outside of handle 162 to facilitate the selective application of manual force against the side wall of handle 162, causing it to flex sufficiently to cause fracturing of the relatively rigid sidewalls of ampule 180, thereby releasing cleaning and disinfecting fluid 182 to flow downwardly by gravity into flexible insert 188.

Referring to FIGS. 28-34, according to another preferred embodiment of the invention, a tool 200 for contacting and/or applying a fluid to attachment surfaces of fluid connector devices used in medical applications is provided that comprises a generally cylindrical housing 202 having two distinct cavities with open ends and with an opening 228 establishing fluid communication between them. A flexible insert 204 is desirably secured to the inside wall of the forwardly facing cavity by use of an adhesive or other similarly effective means. Substantially cylindrical fluid receptacle 212 having a closed rearwardly facing end and an open forwardly facing end sealed with a removable stopper 216 slidably engages the open end of the upper cavity. Fluid receptacle 212 is preferably made of plastic but, alternatively, can be made of a different material, such as glass. Removable stopper 216 is preferably made of a rubber but, alternatively, can be made of another similarly effective polymeric material, cork, or a rupturable membrane that is substantially impermeable to the liquid contained in receptacle 212. Housing 202 and fluid receptacle 212 are desirably cooperatively configured so that an application of manual force against the closed, rearwardly facing end of receptacle 212 will cause stopper 216 to be dislodged from the opening at the lower end upon contact with prongs 230, 232, which can be of the same or different lengths. When stopper 216 is dislodged, a cleaning and disinfecting fluid 220 stored in the receptacle can flow through opening 228 between the two cavities of housing 202 to saturate flexible insert 204 prior to contacting the insert with the frontal attachment to be cleaned. A removable flexible seal or cover 206 is desirably provided over flange 208 at the open end of the forwardly facing cavity of housing 202 to prevent inadvertent contamination of flexible insert 204 prior to use.

Figure 32:
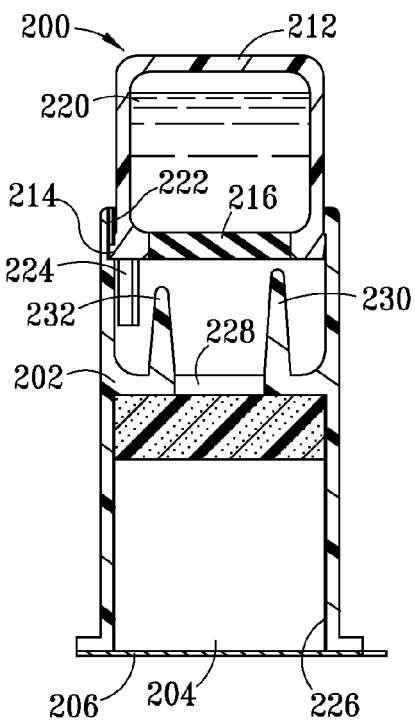
FIG. 32 is a cross-sectional front elevation view of the cleaning tool of FIG. 28 prior to use.
Figure 33:
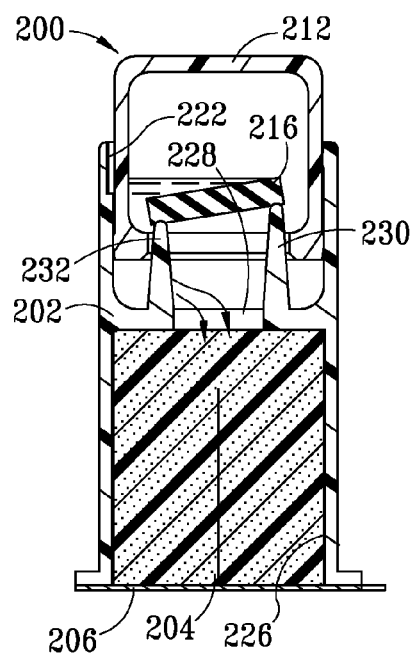
FIG. 33 is a cross-sectional front elevation view of the cleaning tool of FIG. 28 after the fluid receptacle is depressed relative to the housing to dislodge the stopper and release the cleaning and disinfecting fluid.
Figure 34:
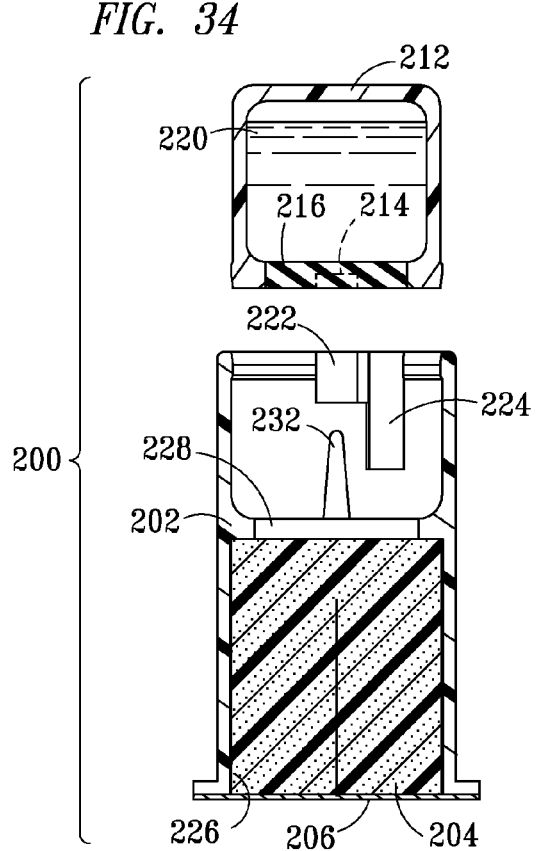
FIG. 34 is a cross-sectional front elevation view taken along line 34-34 of FIG. 31, in which the fluid receptacle is exploded upwardly relative to the housing.

Referring particularly to FIGS. 31-33, prongs 230, 232 or one or more other similarly effective structural members are desirably provided in the rearwardly facing cavity of housing 202 to assist in dislodging stopper 216 from its normal sealing position across the opening at the bottom of fluid receptacle 212 when receptacle 212 is moved forwardly relative to housing 202. The use of one longer prong 230 at one side of stopper 216 is particularly preferred because it concentrates the manual force being applied downwardly on receptacle 212 on a limited area to assist in dislodging stopper 216 to release cleaning and disinfectant 220 to flow through opening 228 into the porous, spongy flexible insert 204. When two or more prongs 230, 232 are used, a combination of one longer prong with the remainder of the prongs being spaced apart circumferentially and slightly shorter than the first will help maintain stopper 216 in a nearly horizontal position, thereby causing stopper 216 to function as a piston that will help force released liquid that has moved past stopper 216 through opening 228 and into flexible insert 204.

Referring particularly to FIGS. 29 and 31-34, according to a particularly preferred embodiment of the invention, structure is provided that prevents fluid receptacle 212 from being depressed relative to housing 202 prematurely, thereby causing stopper 216 to be dislodged from the opening at the bottom end of receptacle 212, until such time as it is desired to saturate flexible insert 204. The rear cavity of housing 202 preferably further comprises two parallel, longitudinally extending slots 222, 224 that cooperate with lug 214 on the lower circumference of receptacle 212 to allow receptacle 212 to be fully depressed only when lug 214 of receptacle 212 is rotationally aligned with longer channel 224. This is desirably achieved by rotating receptacle 212 slightly while grasping housing 202 with the other hand to reposition lug 214 from alignment with channel 222 into alignment with longer channel 224.

Figure 35:
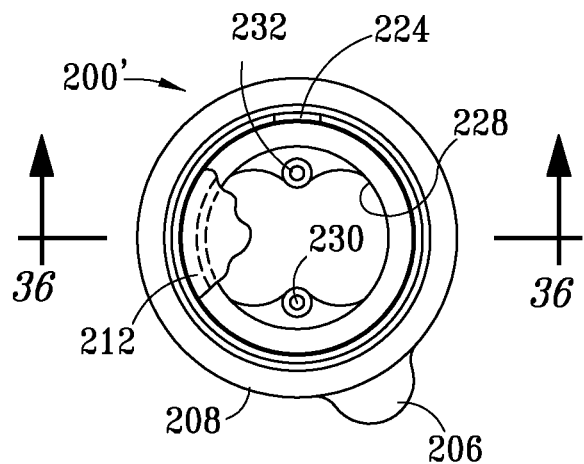
FIG. 35 is a top plan view, partially broken away, of a preferred embodiment of another cleaning tool, having a single longitudinally extending slot in the housing.
Figure 36:
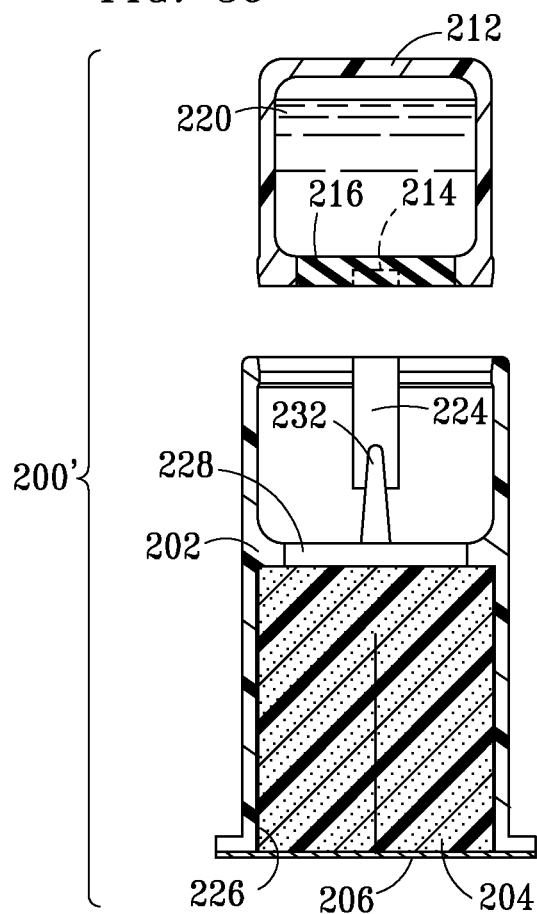
FIG. 36 is a cross-sectional front elevation view taken along line 36-36 of FIG. 35, in which the fluid receptacle is exploded upwardly relative to the housing.
Figure 37:
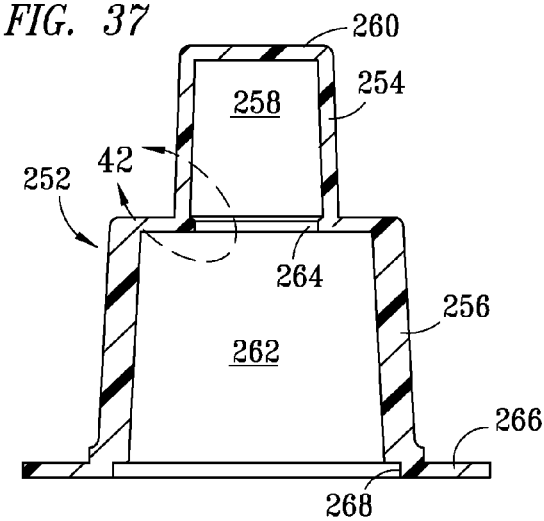
FIG. 37 is a cross-sectional front elevation view of the housing of a preferred embodiment of another cleaning tool of the invention.

Referring to FIGS. 35 and 36, a cleaning tool 200' is disclosed that is in all respects like that previously described in relation to FIGS. 28-34 except that it has only a single longitudinally extending slot 224 and does not include shorter slot 222 as described in relation to the embodiment of FIGS. 28-34. Accordingly, receptacle 212 is not rotatable relative to housing 202, and the tool is activated by forcing receptacle 212 toward prongs 230, 232 until closure 216 is displaced, allowing fluid 220 to flow into flexible insert 204. Cleaning tool 200' is then ready for use when flexible seal or cover 206 is removed.

Referring to FIGS. 37-43, another preferred embodiment of the invention is disclosed wherein cleaning tool 252 comprises a unitary housing with upper and lower sections 254, 256, respectively. Upper section 254 defines cavity 258 having a closed end 260 and an open end defined by annular collar 264. Collar 264 preferably has tapered shoulders 282, 283 (seen in FIG. 42) to facilitate introduction and removal of a tool during molding of the housing, and to facilitate placement and removal of closure 270. Lower section 256 comprises cavity 262 having a bottom opening with an annular flange 266 that further comprises an annular recess 268. Housing 252 is desirably unitarily molded from any suitable polymeric resin and is then inverted to introduce cleaning and/or disinfecting liquid 274 into cavity 258. Because liquids are substantially incompressible, sufficient headspace should be left unfilled in cavity 258 to permit the subsequent disengagement of closure 270 from collar 264 as described below.

After liquid 274 is in place inside cavity 258, removable closure 270 is desirably installed to seal the opening defined by annular collar 264. Removable closure 270 is preferably made of an elastomeric or compressible polymeric material to provide a fluid-tight seal when engaged with annular collar 264. Although the use of a removable closure is preferred, it should be understood that any similarly effective means for sealing liquid 274 into cavity 258 can likewise be used provided that it can be perforated, dislodged or otherwise modified to permit the release of liquid 258 prior to use of tool 252. Following installation of closure 270, flexible insert 276 is desirably inserted into cavity 262 of lower section 256, and is attached to the inside wall of lower section 256 by heat-staking or by other known attachment methods that will serve to resist rotation of the outside wall of flexible insert 276 inside lower section 256.

Figure 40:
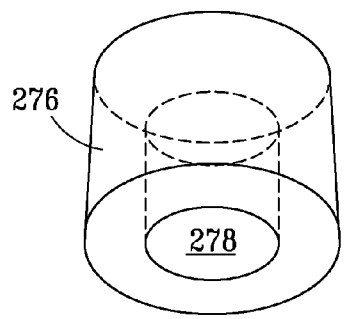
FIG. 40 is a bottom perspective view of the flexible insert of FIG. 39.
Figure 39:
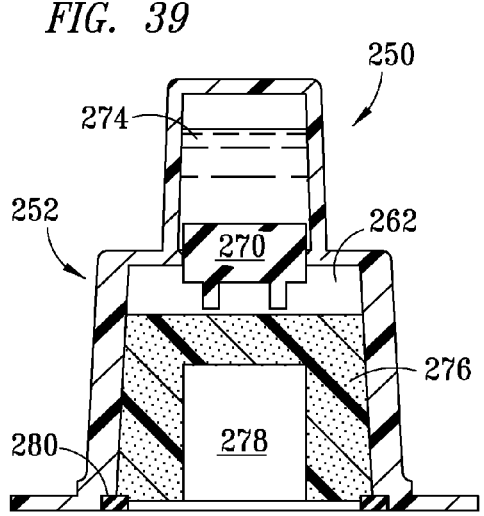
FIG. 39 is a is a cross-sectional front elevation view of a preferred embodiment of another cleaning tool of the invention, comprising the housing of FIG. 37 and the cleaning fluid and closure of FIG. 38, with an absorbent flexible insert disposed inside the portion of the housing below the closure.

Flexible insert 276 is preferably made from a cellular polymeric material having sufficient porosity or liquid-retaining capability to receive and hold liquid 274 flowing into cavity 262 from cavity 258 following displacement of closure 270, and also having the ability to release or discharge liquid 274 onto an attachment surface of a fluid connector with which flexible insert 276 is placed in contact during use of cleaning tool 252. As shown in FIGS. 39 and 40, flexible inert 276 preferably further comprises a cylindrical recess 278 that is configured to receive the attachment end of a fluid connector device for cleaning and/or disinfecting during use of tool 252. Flexible insert can be held in place by a retainer ring 280 insertable into annular recess 268, although the use of such a retainer ring is not required if flexible insert 276 is attached to the inside of lower section 256 as previously described. Although not shown in FIG. 29, it will be appreciated that a seal or cover as previously described in relation to cover 206 of FIGS. 32-34, 36 is desirably applied across the open end of lower section 256 following assembly of tool 252 as described above. Such a seal or cover will maintain the open end of tool 252 in a sanitary condition until removed just prior to use, and can be conveniently attached by pressure-sensitive adhesive or the like to the underside of flange 266. Where tool 252 is entirely packaged inside a sanitary wrap, the use of another seal or cover across the opening of lower section 256 is not needed.

Figure 38:
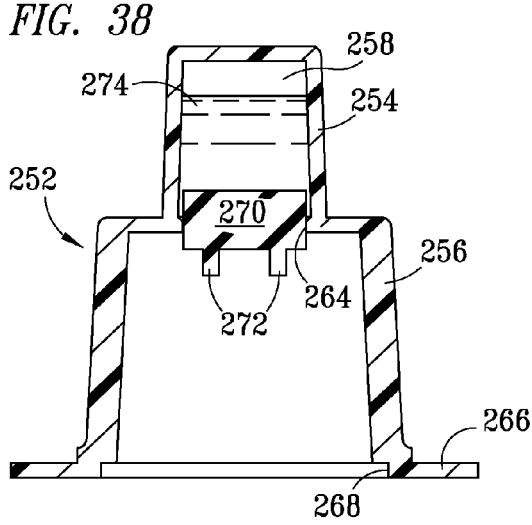
FIG. 38 is a cross-sectional front elevation view of the housing of FIG. 37, with a cleaning fluid disposed inside a receptacle in the housing and a closure sealing the opening of the receptacle.
Figure 41:
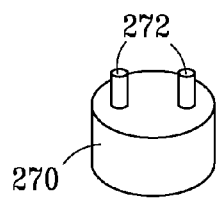
FIG. 41 is bottom perspective view of the closure of FIGS. 38 and 39.
Figure 42:
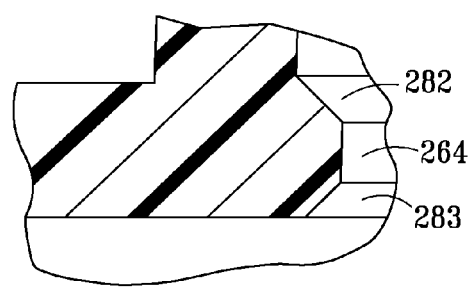
FIG. 42 is an enlarged detail view taken from a position substantially as shown in FIG. 37.

To use cleaning tool 252, following removal of the sanitary wrap or cover, the free end of the fluid connector device having the attachment surfaces to be cleaned is desirably inserted into recess 278 of flexible insert 276, and is forced upwardly, causing the upper surface of flexible insert 276 to contact prongs 272 of closure 270, best seen in FIGS. 38 and 41. The continued application of upwardly directed force to the fluid connector will displace closure 270, thereby releasing cleaning and/or disinfecting fluid 274 downwardly into flexible insert 276. The configuration of prongs 272 and the material used to make them are desirably such that they will transmit to the body of closure 270 enough force to displace closure 270 from the opening defined by annular collar 264. Alternatively, closure 284 having a single projection 286 with a slightly stepped-in diameter relative to body 288 can be substituted for closure 270 if desired.

Figure 43:
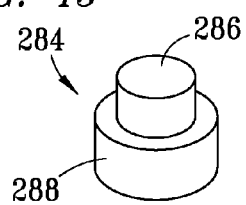
FIG. 43 is a bottom perspective view of another closure as shown in FIGS. 44-46.
Figure 49:
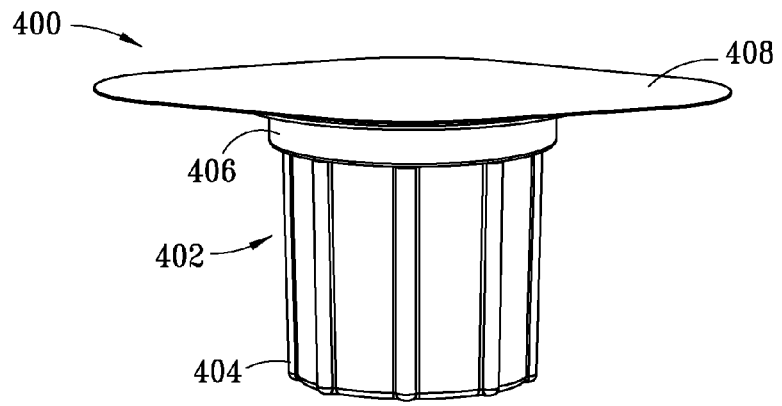
FIG. 49 is a top perspective view of a preferred embodiment of another cleaning tool of the invention.
Figure 50:
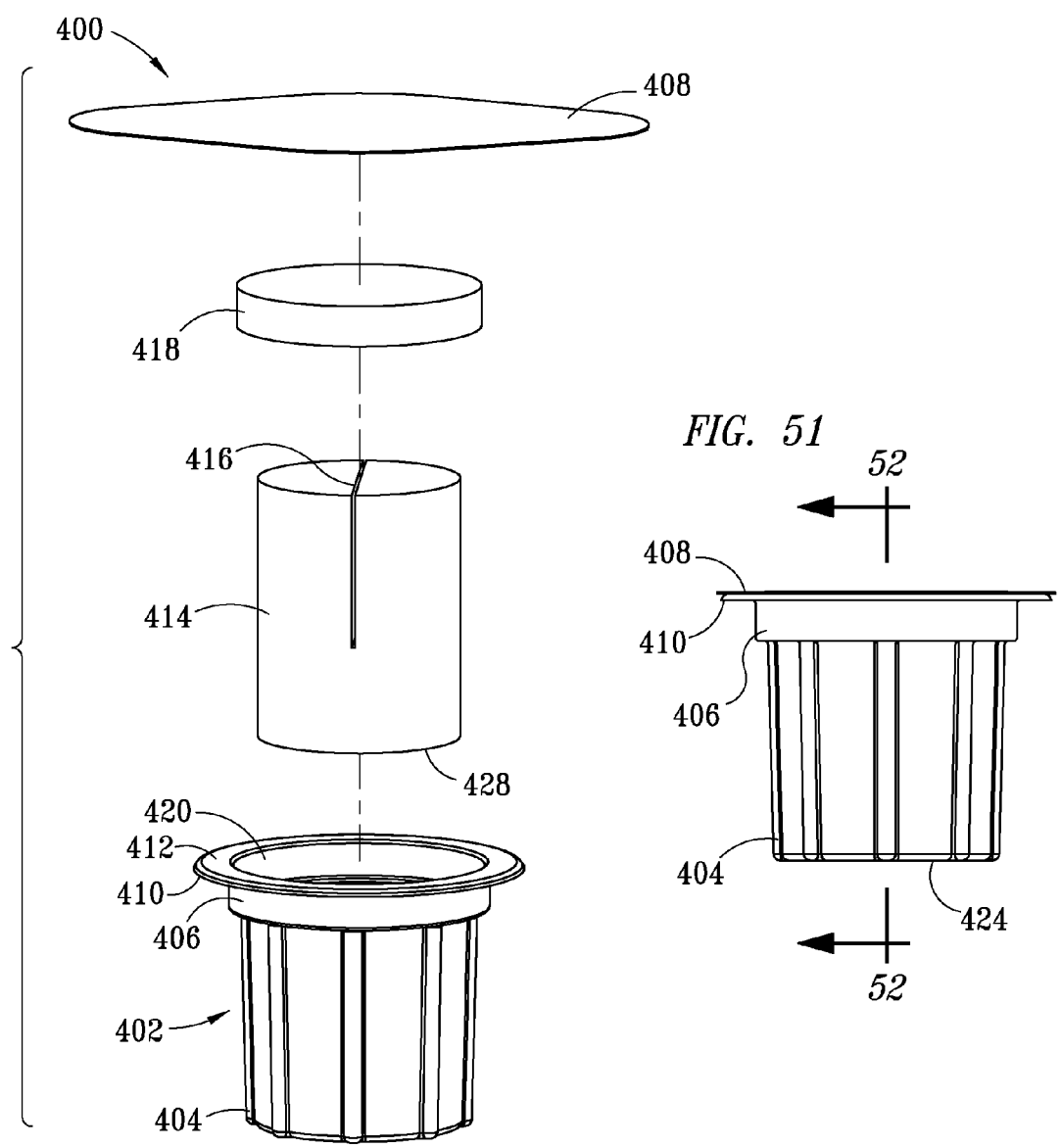
FIG. 50 is an exploded view of the cleaning tool of FIG. 49.
Figure 51:
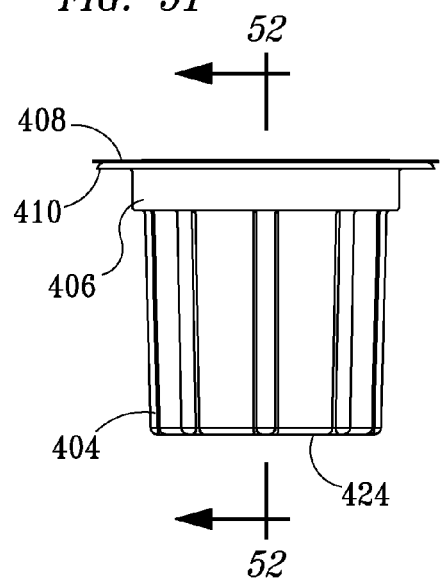
FIG. 51 is front elevation view of the cleaning tool of FIG. 49.
Figure 52:
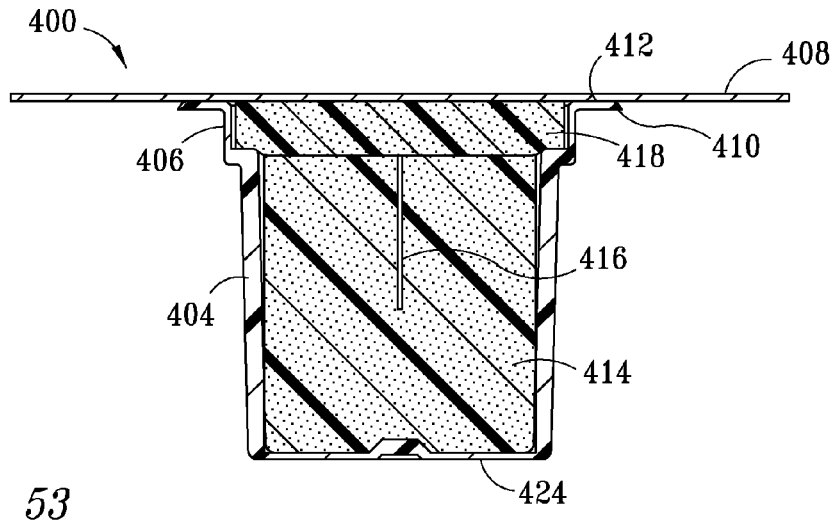
FIG. 52 is an enlarged cross-sectional view taken along FIG. 52-52 of FIG. 51.
Figure 53:
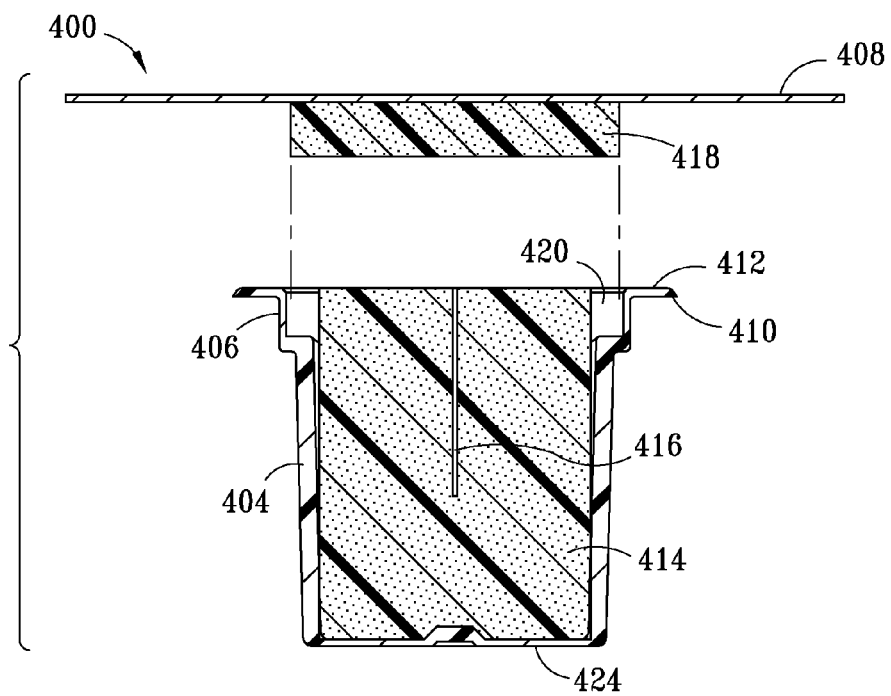
FIG. 53 is an exploded view as in FIG. 52 but showing the closure web and attached disk-shaped flexible insert displaced above the housing and another substantially cylindrical flexible insert.
Figure 54:
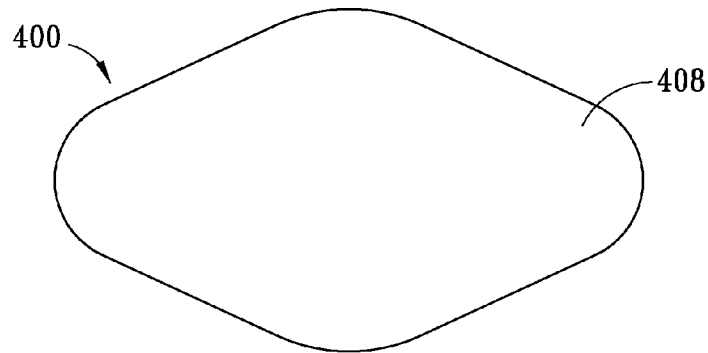
FIG. 54 is a top view of the cleaning tool of FIG. 49.

Referring to FIGS. 44-47, another cleaning tool 300 is disclosed that is made similarly to tool 252 of FIGS. 37-42, but utilizes a stopper 314 made as shown in FIG. 43. Tool 300 comprises housing 302 with upper section 304 having a closed end 306, and a lower section 308 having annular flange 310 at its base, and an annular recess 324 inside flange 310. In this embodiment, flexible insert 320 is made as shown in FIG. 47, with a larger-diameter base 338 and a transverse slit 322 extending upwardly into, but not through the top of body section 340. Referring to FIG. 46, when flexible insert 320 is made with a slit 322 instead of a recess 278 as shown in FIG. 39, attachment surfaces such as threads 336 of fluid connector 328, here attached to a fluid flow line 334, can be forced upwardly into slit 322, causing top surface 332 to contact and displace closure 314. This in turn allows cleaning and/or disinfecting liquid 316 as previously described to flow downwardly as indicated by arrows 330 to saturate flexible insert 320. Attachment surfaces 336 of fluid connector 328 are then cleaned by moving tool 300 both axially and rotationally in relation to fluid connector 328.

Referring to FIG. 48, cleaning tool 350 is another embodiment of the invention wherein a flexible insert 362 made as described in relation to FIGS. 44-47. In this embodiment, housing 352 has substantially parallel inside and outside walls that continue from flange 356 to closed end 354 of the upper cavity. Annular collar 358 is desirably made substantially as described in relation to FIG. 42 to facilitate insertion and removal of a core pin in the molding tool (not shown) and to facilitate installation and displacement of closure 360. In this embodiment, fluid 364 must again have sufficient headspace to allow displacement of closure 360. However, where closure 360 is a membrane that is ruptured, torn or perforated, little if any headspace is required.

Referring to FIGS. 49-54, another cleaning tool 400 is disclosed that comprises housing 402 having one closed end 424 and an oppositely disposed open end with a fluted, substantially cylindrical, sidewall 404 disposed therebetween, the sidewall 404 further comprising a larger diameter annular sidewall section 406 defining an annular recess 420 and an annular flange 410 with substantially flat annular sealing surface 412 disposed adjacent to the open end. A first flexible polymeric foam insert 414 capable of absorbing and subsequently expelling liquid cleaner is desirably anchored inside housing 402 in such manner that insert 414 cannot be rotated freely inside housing 402 during use. An opening such as slit 416 is preferably provided in the end of insert 414 that faces outwardly from housing 402. A second flexible foam insert 418 having a diameter slightly larger than that of insert 414 and a thickness such that insert 418 can be received inside annular recess 420 when compressed is preferably attached to the underside of flexible, fluid impermeable web 408 in a position aligned with annular recess 420 of housing 402. Web 408 serves as a removable closure or cover for cleaning tool 400 after a liquid suitable for cleaning and/or disinfectant use for medical devices has been introduced into housing 402, where the liquid is absorbed into foamed inserts 414 and 418. Web 408 is desirably releasably attached to flange surface 412 of housing 402 by a releasable adhesive that provides a satisfactory liquid-tight seal between housing 402 and web 408. If desired, a label or other printed indicia can be applied to the outwardly facing surface of web 408, said surface being shown in FIG. 54. Upon removal of web 408 just prior to use, the liquid-containing disk-shaped insert 418 attached to the underside of the web can be used for topical cleaning of skin, an exposed surface of an object, or an attachment surface of a fluid connector as desired in addition to use of the liquid-containing flexible insert 414 disposed inside the housing.

Referring to FIGS. 55-59, another cleaning tool 500 is disclosed that can be used for both topical cleaning of skin or an exposed surface, and for mechanically cleaning and/or applying fluid to attachment surfaces of fluid connector devices used in medical applications. Cleaning tool 500 preferably comprises structural elements substantially as described in Paragraph 0041 above, including housing 502 with closed end 524, annular sidewall section 506 defining annular recess 520, annular flange 510 with annular sealing surface 512, and flexible, fluid-tight closure 508. The outside diameter of flange 510 is desirably sufficient great to shield insert 514 from direct contact with the fingers of the user, but not so great as to create interference with branched structures that are part of the device to be cleaned. Cleaning tool 500 differs from cleaning tool 400 discussed above in that tool 500 preferably comprises only a single, liquid-absorbing, flexible, compressible foamed polymeric insert 514 having a cylindrical base 530, bottom 534, sidewall 528, and a top surface 532 that preferably comprises recess 516. Cylindrical base 530 of insert 514 is preferably heat-staked inside of, or otherwise attached in fixed relation to, annular recess 520 of housing 502. Recess 516 in upwardly projecting portion of insert 516 is desirably provided to facilitate use as a cleaning tool for attachment surfaces of fluid connector devices used in medical applications. Prior to heat-staking insert 514 in place relative to housing 502, a cleaning and/or disinfecting liquid 536 is desirably introduced into the interior space 538 of the housing. Prior to sealing with web closure 508, insert projects upwardly past the otherwise open end of the housing substantially as shown in FIG. 59, except that the level of cleaning liquid 536 is typically as shown in FIG. 58 prior to saturating insert 514. Referring to FIG. 58 after attachment of insert 514 to annular recess 520 of housing 502, the flexible foam insert is desirably compressed inside the housing and web 508 is releasably sealed to sealing surface 512 (FIG. 59) of flange 510 to cover the opening and maintain insert 514 in its compressed state pending use. When web closure 508 is later removed by application of force as indicated by 542 (FIG. 59) just prior to use, and the insert is substantially saturated with the cleaning liquid, as it will typically be during shipment and handling prior to use, insert 514 expands again to its projecting position to facilitate use as a topical cleaning or disinfecting tool. Recess 516 in the upwardly facing portion of insert 514 can receive at least a portion of the attachment surfaces of a fluid connector or such other device to be cleaned, and the upwardly projecting portion of insert 514 can be forced back down inside housing 502, where sidewalls 504 provide resistance and facilitate scrubbing the attachment surfaces. Recess 516 can be formed by melting or burning a hole into insert 514 or another similarly effective means such as drilling. Also, a rod can be pressed upwardly from the bottom of insert 514 prior to attachment to housing 502, and a cone or cylinder of the foamed material will project upwardly from surface 532 (FIG. 57) and can be clipped away. When the rod is removed, a recess 516 will thereby be formed that is visible and accessible in and below surface 532.

Figure 55:
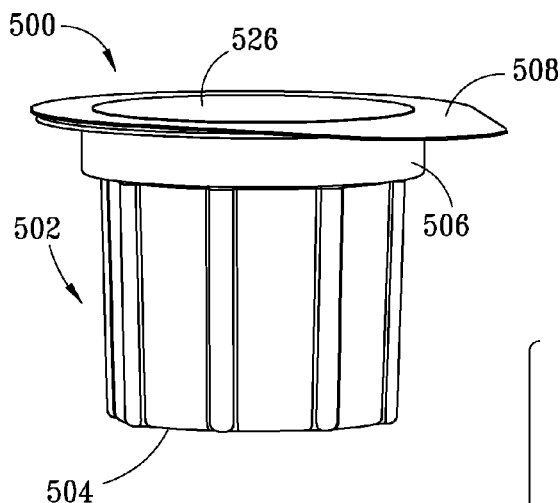
FIG. 55 is a top perspective view of a preferred embodiment of another cleaning tool of the invention.
Figure 56:
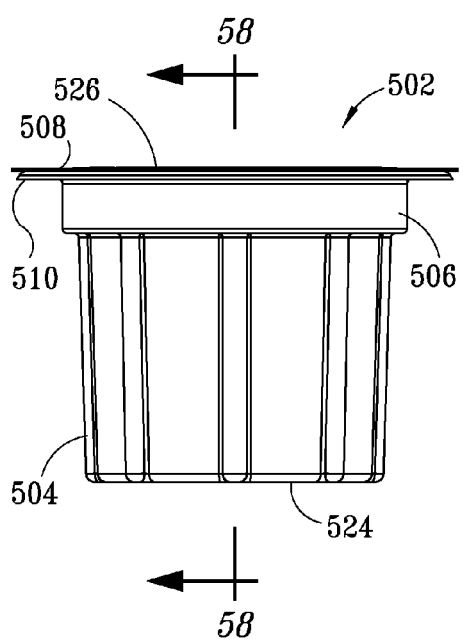
FIG. 56 is a front elevation view of the cleaning tool of FIG. 55.
Figure 57:
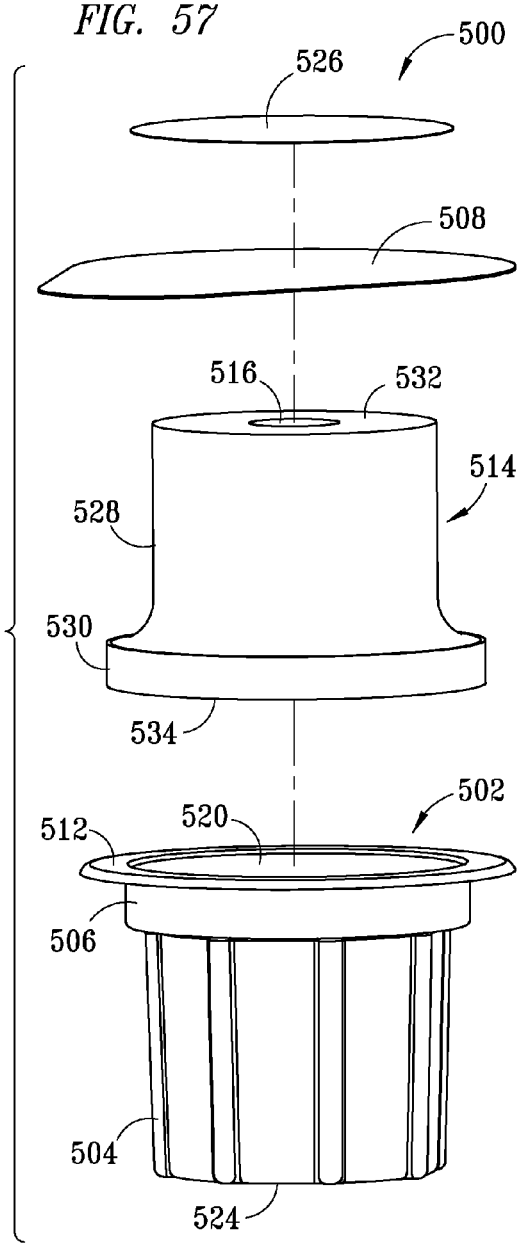
FIG. 57 is an exploded view of the cleaning tool of FIG. 55.

It will be apparent to those of ordinary skill in the art upon reading this disclosure that the protruding insert 514 facilitates use of cleaning tool 500 as a skin-prep tool as well as for cleaning attachment surfaces of a device. Because insert 514 is anchored inside housing 502, rotation of insert 514 inside housing 502 is limited, and frictional contact between insert 514 and an attachment surface is enhanced. Furthermore, recess 516 serves as guide for the insertion of a fluid connector into tool 500 for cleaning. Tool 500 serves well for cleaning external threads of a fluid connector or other device, and flange 510 shields the user's fingers from contacting and possibly contaminating either insert 514 or the attachment surfaces being cleaned. The open space in housing 502 below annular recess 520 allows insert 514 to be compressed sufficiently inside housing 502 to produce a substantially flat seal by web 508, and also allows for variable compression inside housing 502 during use. Referring to FIGS. 55-57, web closure 508 can optionally include an outwardly facing label 526 having desired indicia printed on it. Web closure 508 preferably comprises at least one portion extending outwardly beyond flange 510 that is manually graspable to facilitate removal from housing 502 prior to use.

The absence of lateral support above recess 520 and flange 510 makes it easier to push insert 514 inside housing 502 prior to sealing, and also facilitates disengagement and removal of a cleaned device following use because the device can pull insert 514 back outside housing 502, again relieving the lateral support that may otherwise be holding the walls of recess 516 against threads or other attachment surfaces of the device. More available space within housing 502 also allows the use of more cleaning liquid during assembly.

It will be appreciated that the cleaning tools of the invention are desirably packaged and sterilized so that they will remain sterile until removed from the packages immediately prior to use. Desirably, where the cleaning tool is shipped and stored with a flexible insert that is already at least partially saturated with a cleaning and disinfecting fluid, a barrier material should be used as part of the packaging treatment to further insure that the fluid does not evaporate prior to use.

Other alterations and modifications of the invention disclosed herein will likewise become apparent to those of ordinary skill in the art upon reading this disclosure, and it is intended that the scope of the invention be limited only by the broadest interpretation of the appended claims to which the inventors are legally entitled.

What is claimed is:

1. A tool useful for contacting and applying a liquid cleaner to attachment surfaces of a fluid connector device used in medical applications, the connector device having laterally facing surfaces, the tool comprising:
   a housing with a substantially cylindrical or polygonal inside wall, an open end having a defined shape during storage and use, a closed end opposite the open end, and two cavities separated by an annular collar;
   a flexible, porous cellular insert disposed inside the housing, the insert conforming substantially to a portion of the inside wall and comprising a recess having an opening facing the open end and a recess side wall facing radially inward to receive and contact the laterally facing surfaces of the connector device, the flexible insert containing the cleaner prior to contacting the attachment surfaces and being sufficiently compressible against the attachment surfaces to discharge some of said cleaner against said attachment surfaces during use.

2. The tool of claim 1 wherein the cleaner also disinfects the attachment surfaces.

3. The tool of claim 2 wherein the cleaner is selected from the group consisting of liquids including alcohol and chlorhexidine.

4. The tool of claim 1 wherein the flexible insert is attached to the housing.

5. The tool of claim 1 wherein one cavity has a closed end that is part of the housing.

6. The tool of claim 1 wherein the open end of the housing is covered by a removable closure prior to use.

7. The tool of claim 1 wherein the inside wall has sections with different diameters.

8. The tool of claim 1 wherein the inside wall comprises a tapered section.

9. The tool of claim 6 wherein the removable closure comprises at least one projection.

10. The tool of claim 1, further comprising a releasable closure and a projection engageable with the flexible insert.

11. A tool useful for cleaning and disinfecting attachment surfaces of a fluid connector device used in medical applications, the tool further comprising a housing having an open end; a compressible, a liquid-absorbing polymeric insert comprising an outwardly facing recess and having a portion that is fixed to the housing; a cleaning liquid disposed inside the housing; and a releasable cover sealed over an opening in the housing;

at least a portion of the foam insert being expandable outside the housing following release of the cover from over the opening.

12. A tool useful for cleaning and/or disinfecting attachment surfaces of a fluid connector device used in medical applications, the tool further comprising:

a housing having a body with a substantially cylindrical or polygonal inside wall, an open end having a defined shape, a closed end, an annular recess disposed near the open end, and an annular flange disposed around the open end;

a flexible insert comprising an outwardly facing recess, the insert being seated in substantially fixed rotational relation to the annular recess, said insert projecting outwardly from the open end when in a relaxed state but being compressible inside the housing during manufacture, the flexible insert carrying or containing a composition selected from the group consisting of cleaning agents and disinfectants, and being configured and sufficiently compressible to receive, contact, clean and disinfect the attachment surfaces; and a liquid impermeable, flexible closure releasably sealing the insert and composition inside the housing prior to use.

13. The tool of claim 12 wherein the flexible insert is heat-staked inside the housing.

14. The tool of claim 12 wherein the housing comprises sidewall sections that are fluted.

15. The tool of claim 12 wherein the housing comprises sidewall sections that are substantially cylindrical, but are outwardly tapered between the closed and open ends of the housing.

16. The tool of claim 12 wherein the insert comprises a compressible polymeric foam capable of absorbing a liquid upon contact with the liquid and capable of expelling a liquid upon compression against a rigid surface.

17. The tool of claim 12 wherein the flexible closure comprises an outwardly projecting, manually graspable portion that extends beyond the flange.

* * * * *